(12) United States Patent
Ihara et al.

(10) Patent No.: US 12,201,461 B2
(45) Date of Patent: Jan. 21, 2025

(54) CEREBRAL INFARCTION TREATMENT SUPPORT SYSTEM

(71) Applicants: NATIONAL CEREBRAL AND CARDIOVASCULAR CENTER, Suita (JP); SHIMADZU CORPORATION, Kyoto (JP)

(72) Inventors: Masafumi Ihara, Suita (JP); Takeshi Yoshimoto, Suita (JP); Daisuke Kawakami, Kyoto (JP)

(73) Assignees: NATIONAL CEREBRAL AND CARDIOVASCULAR CENTER, Suita (JP); SHIMADZU CORPORATION, Kyoto (JP)

( * ) Notice: Subject to any disclaimer, the term of this patent is extended or adjusted under 35 U.S.C. 154(b) by 277 days.

(21) Appl. No.: 17/770,374

(22) PCT Filed: Oct. 28, 2020

(86) PCT No.: PCT/JP2020/040517
§ 371 (c)(1),
(2) Date: Apr. 20, 2022

(87) PCT Pub. No.: WO2021/085505
PCT Pub. Date: May 6, 2021

(65) Prior Publication Data
US 2022/0401043 A1    Dec. 22, 2022

(30) Foreign Application Priority Data
Oct. 29, 2019 (JP) .................................. 2019-195879

(51) Int. Cl.
*A61B 6/03* (2006.01)
*A61B 5/055* (2006.01)

(52) U.S. Cl.
CPC ................ *A61B 6/03* (2013.01); *A61B 5/055* (2013.01)

(58) Field of Classification Search
CPC .. A61B 6/03; A61B 5/055; A61B 6/00; A61B 6/377; A61B 5/00; A61B 5/377; G01N 33/50
See application file for complete search history.

(56) References Cited

U.S. PATENT DOCUMENTS

2005/0113680 A1    5/2005 Ikeda et al.
2015/0097868 A1    4/2015 Banerjee et al.
(Continued)

FOREIGN PATENT DOCUMENTS

JP    2004290240 A   * 10/2004
JP    4509531 B2      7/2010
(Continued)

OTHER PUBLICATIONS

Korean Office Action issued Apr. 4, 2024 in Application No. 10-2022-7017151.
(Continued)

*Primary Examiner* — David P Porta
*Assistant Examiner* — Fani Polyzos Boosalis
(74) *Attorney, Agent, or Firm* — Sughrue Mion, PLLC

(57) ABSTRACT

A cerebral infarction treatment support system (100) includes a detection device (10), a display (30), and an image controller (20), and the image controller (20) includes a receiver (21) configured to receive at least one of first information (41) generated by the detection device (10) or second information (42) related to a susceptibility gene generated based on the first information (41), and a video output (22) configured to output at least one of the received first information (41) or second information (42) to the display (30).

14 Claims, 13 Drawing Sheets

(56) References Cited

U.S. PATENT DOCUMENTS

| | | |
|---|---|---|
| 2016/0067007 A1 | 3/2016 | Piron et al. |
| 2019/0027254 A1 | 1/2019 | Li et al. |
| 2019/0183445 A1 | 6/2019 | Okuno et al. |

FOREIGN PATENT DOCUMENTS

| | | | |
|---|---|---|---|
| JP | 2010259390 A | * | 11/2010 |
| JP | 2016-059759 A | | 4/2016 |
| JP | 2016-073542 A | | 5/2016 |
| JP | 5989354 B2 | | 9/2016 |
| JP | 2019-21136 A | | 2/2019 |
| JP | 2021069466 A | * | 5/2021 |

OTHER PUBLICATIONS

Journal of Clinical Laboratory Medicine, Jan. 2019, pp. 30-31, vol. 63, No. 1.

Daisuke Kawakami, "Development of RNF213 rapid genotyping system for moyamoya Disease", Medical Science Digest, Mar. 2019 issue (on-sale date: Feb. 20, 2019); pp. 6-8, vol. 45, No. 3.

International Search Report for PCT/JP2020/040517 dated Dec. 15, 2020 (PCT/ISA/210).

Written Opinion for PCT/JP2020/040517 dated Dec. 15, 2020 (PCT/ISA/237).

Extended European Search Report dated Nov. 8, 2023 in European Application No. 20881310.5.

Office Action received in Chinese Application No. 202080068411.8, mailed Jul. 27, 2024.

Office Action received in Japanese Application No. 2023-191751, mailed Oct. 22, 2024.

Satoru Miyawaki, et al; "Genetic analysis of intracranial major artery stenosis: Analysis of moyamoya disease associated gene *RNF213*"; Cerebral Blood Flow and Metabolism; 2017, Co. 28, No. 2; pp. 341-345.

Communication issued Nov. 26, 2024, in Korean Patent Application No. 10-2022-7017151.

* cited by examiner

FIG.6

| PATIENT INFORMATION | 0123456789ABC | ←45 |
|---|---|---|
| FIRST INFORMATION | RNF213 p.R4810K GENETIC POLYMORPHISM IS PRESENT | ←41 |
| SECOND INFORMATION — TYPE OF CEREBRAL INFARCTION | MORE LIKELY TO BE ATHEROTHROMBOTIC CEREBRAL INFARCTION | ←42a,42 |
| SECOND INFORMATION — INFORMATION ABOUT CEREBRAL BLOOD VESSEL | VASCULAR DIAMETER MAY BE SMALL | ←42b,42 |
| SECOND INFORMATION — RECOMMENDED/ DEPRECATED DEVICE | <RECOMMENDED> THROMBUS SUCTION DEVICE <DEPRECATED> THROMBUS RETRIEVAL DEVICE | ←42c,42 |

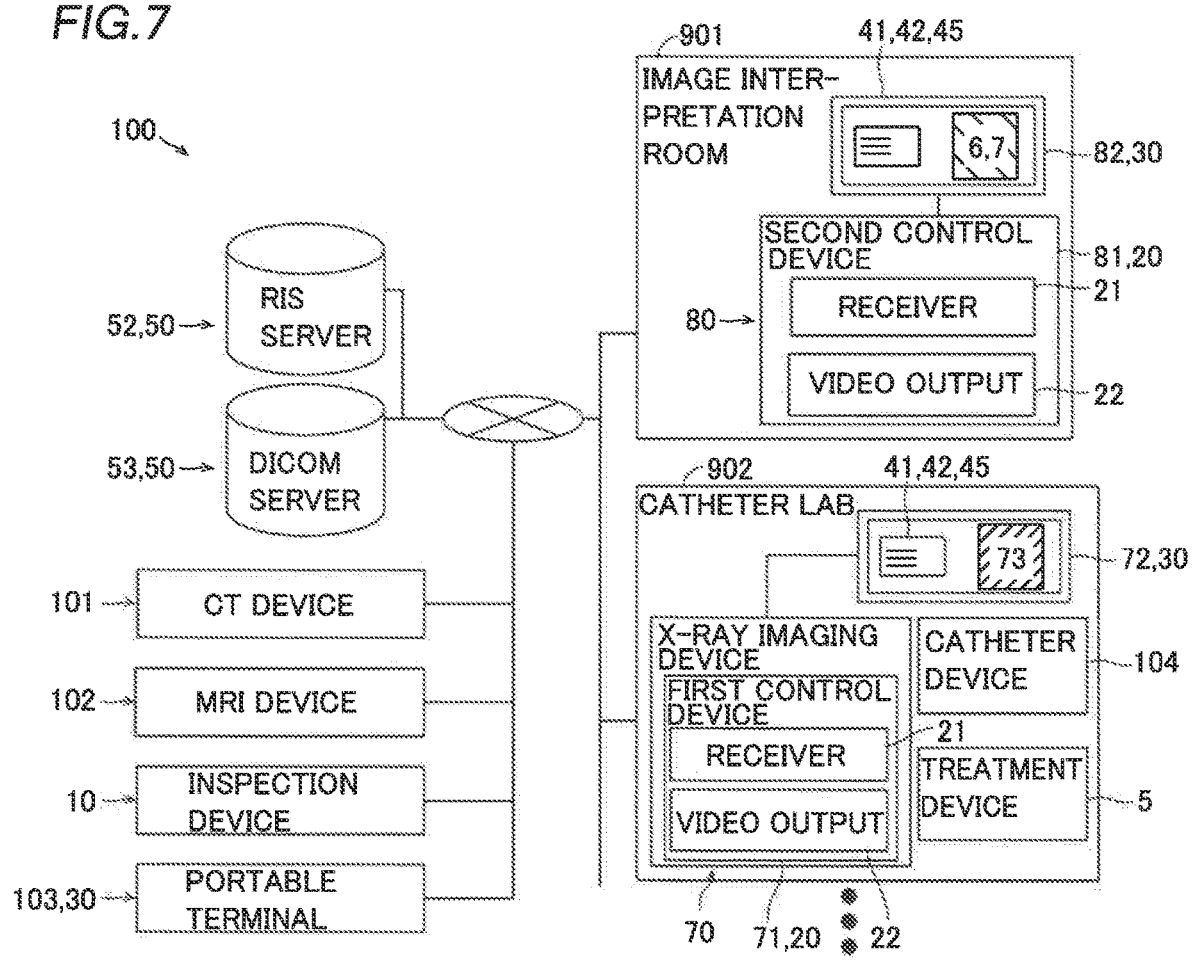

FIG.7

FIG.18
(a)
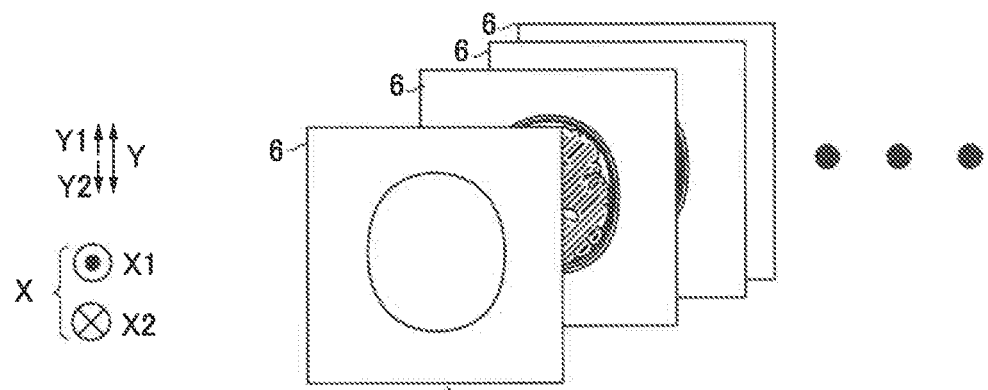
(b)
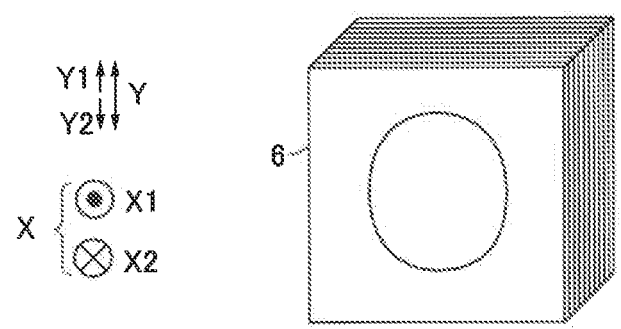
(c)
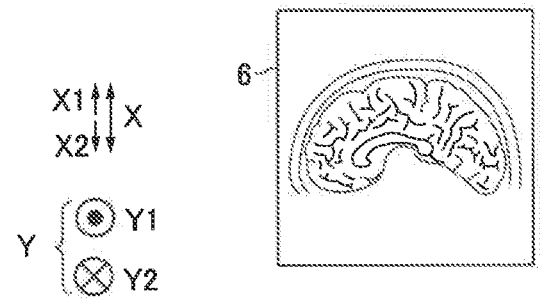

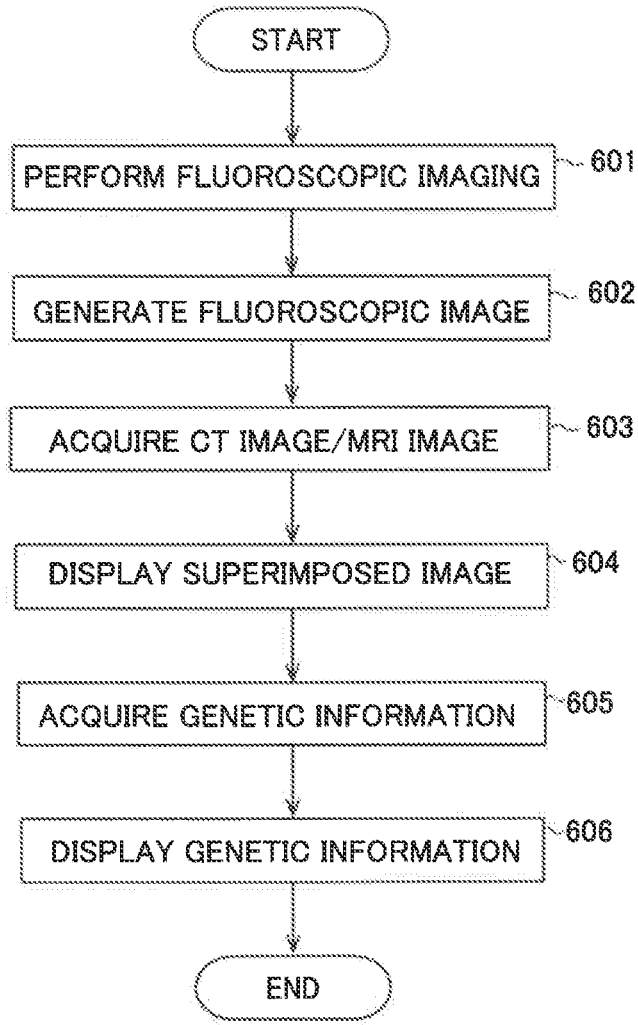

CEREBRAL INFARCTION TREATMENT SUPPORT SYSTEM

CROSS REFERENCE TO RELATED APPLICATIONS

This application is a National Stage of International Application No. PCT/JP2020/040517 filed Oct. 28, 2020, claiming priority based on Japanese Patent Application No. 2019-195879 filed Oct. 29, 2019.

TECHNICAL FIELD

The present invention relates to a cerebral infarction treatment support system and a cerebral infarction treatment support method, and more particularly, it relates to a cerebral infarction treatment support system and a cerebral infarction treatment support method both for supporting the diagnosis and treatment of cerebral infarction patients in the acute phase.

BACKGROUND ART

Conventionally, a device that supports the diagnosis and treatment of cerebral infarction patients in the acute phase is known. Such a device is disclosed in Japanese Patent No. 4509531.

Japanese Patent No. 4509531 discloses an acute cerebral infarction diagnosis and treatment support device incorporated into an X-ray computerized tomographic apparatus. The acute cerebral infarction diagnosis and treatment support device disclosed in U.S. Pat. No. 4,509,531 provides a contrast-enhanced image obtained by performing a threshold process or a clustering process on a CT image obtained by non-contrast-enhanced CT imaging and a cerebral blood flow image obtained by processing continuous images obtained by dynamic CT imaging and quantitatively showing the blood flow dynamics of capillaries in a brain tissue, and superimposes a first ROI identified from the contrast-enhanced image and a second ROI identified from the cerebral blood flow image on the CT image and displays the same.

PRIOR ART

Patent Document

Patent Document 1: Japanese Patent No. 4509531

SUMMARY OF THE INVENTION

Problems to be Solved by the Invention

A patient in the acute phase who has developed cerebral infarction is typically diagnosed and treated according to the following procedures (1) to (4).
  (1) A computed tomography (CT) image as in Japanese Patent No. 4509531 or a magnetic resonance imaging (MRI) image of the patient's head is captured.
  (2) Diagnosis such as determination of the type of cerebral infarction and identification of the location of a thrombus is performed based on the captured image.
  (3) Drug treatment using thrombolytics, for example, to dissolve the thrombus is attempted.
  (4) If necessary, thrombus retrieval by catheter treatment (endovascular treatment) is performed, for example.

The types of cerebral infarction are classified into three types: cardiogenic cerebral embolism, lacunar infarction, and atherothrombotic cerebral infarction. Furthermore, there are a plurality of types of treatment devices used for catheter treatment of cerebral infarction, and they are selected according to the type of cerebral infarction that has been developed.

However, conventionally, the type of cerebral infarction is visually determined by a doctor from a CT image or an MRI image. Thus, skill is required, and it is difficult to identify the type of cerebral infarction. Furthermore, a doctor who has identified the type of cerebral infarction may be different from a doctor who performs catheter treatment. The treatment of cerebral infarction patients is highly urgent, and thus there is no time to prepare documents, etc., and there is a high possibility that the type of cerebral infarction is orally communicated to the doctor who performs the treatment. The certainty is low in oral communication, and there is no means to confirm the type of cerebral infarction again at the time of catheter treatment for selecting a treatment device.

Therefore, apart from image information by CT or MRI, for example, it is desired to enable presentation of support information useful for a doctor to identify the type of cerebral infarction during diagnosis or treatment of cerebral infarction in the acute phase.

The present invention is intended to solve at least one of the above problems. The present invention aims to provide a cerebral infarction treatment support system and a cerebral infarction treatment support method each capable of presenting support information useful for a doctor to identify the type of cerebral infarction during diagnosis or treatment of cerebral infarction in the acute phase.

Means for Solving the Problems

In order to attain the aforementioned object, as a result of earnest studies, the present inventors have found that the presence or absence of a specific human gene significantly correlates with a susceptibility gene for identifying the type of cerebral infarction, and made the following invention. That is, a cerebral infarction treatment support system according to a first aspect of the present invention includes a detection device configured to measure a biological sample collected from a patient, the detection device being configured to generate first information as to whether or not the biological sample has a susceptibility gene for cerebral infarction, a display arranged in at least one of a catheter lab in which a vascular X-ray imaging device is arranged or an image interpretation room in which an image browsing terminal for a radiation diagnostic image or an MRI image is arranged, and an image controller configured or programmed to control the display. The image controller includes a receiver configured to receive at least one of the first information generated by the detection device or second information related to the susceptibility gene generated based on the first information, and a video output configured to output at least one of the received first information or second information to the display.

In this description, the second information is information related to cerebral infarction that can be derived from the first information as to whether or not the susceptibility gene for cerebral infarction is present, and medical scientific knowledge regarding the susceptibility gene.

A cerebral infarction treatment support method according to a second aspect of the present invention includes measuring a biological sample collected from a patient and generating first information as to whether or not the biological sample has a susceptibility gene for cerebral infarction, receiving at least one of the generated first information or second information related to the susceptibility gene generated based on the first information, and outputting at least one of the received first information or second information to a display. The display is arranged in at least one of a catheter lab in which a vascular X-ray imaging device is arranged or an image interpretation room in which an image browsing terminal for a radiation diagnostic image or an MRI image is arranged.

Effect of the Invention

In the cerebral infarction treatment support system according to the first aspect and the cerebral infarction treatment support method according to the second aspect, with the above configuration, in the treatment of a cerebral infarction patient in the acute phase, at least one of the first information as to whether or not the patient has the susceptibility gene for cerebral infarction or the second information generated based on the first information can be displayed on the display arranged in the image interpretation room in which the type of cerebral infarction is determined and the location of a thrombus is identified, for example. Thus, at least one of the first information or the second information is displayed during diagnosis for determining the type of cerebral infarction and identifying the location of the thrombus, for example, such that a doctor can determine the type of cerebral infarction, taking into consideration information based on the presence or absence of the susceptibility gene, which cannot be obtained from image information, in addition to the conventional image interpretation based on a CT image and an MRI image. Furthermore, at least one of the first information or the second information is displayed on the display arranged in the catheter lab in which a patient who has developed cerebral infarction is treated such that a doctor who actually performs treatment can select a treatment device for catheter treatment according to the type of cerebral infarction, taking into consideration the information based on the presence or absence of the susceptibility gene. Thus, it is possible to present support information useful for the doctor to identify the type of cerebral infarction during diagnosis or treatment of cerebral infarction in the acute phase.

BRIEF DESCRIPTION OF THE DRAWINGS

FIG. 6 is a diagram showing examples of first information and the second information FIG. 7 is a diagram showing a configuration example of the cerebral infarction treatment support system.

FIG. 18 at (A) to (C) are diagrams for illustrating reconstruction of vascular image data.

FIG. 19 is a flowchart showing the operation of the vascular imaging device.

MODES FOR CARRYING OUT THE INVENTION

An embodiment embodying the present invention is hereinafter described on the basis of the drawings.

Figure 1:
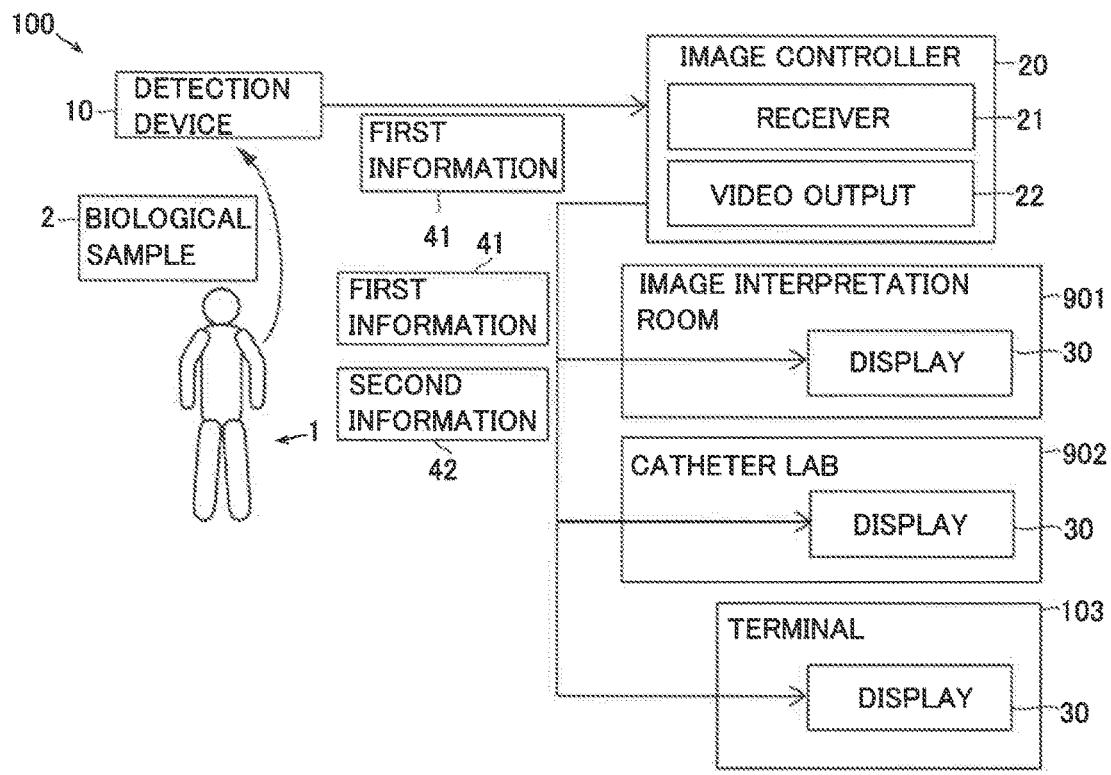
FIG. 1 is a schematic view showing the overall configuration of a cerebral infarction treatment support system.

The configuration of a cerebral infarction treatment support system 100 according to the embodiment is now described with reference to FIG. 1.

The cerebral infarction treatment support system 100 is a system that supports the diagnosis and treatment of cerebral infarction patients in the acute phase. The cerebral infarction treatment support system 100 is provided in a medical facility such as a hospital. The cerebral infarction treatment support system 100 provides a doctor or the like with useful information for diagnosis and treatment when the doctor diagnoses and treats a cerebral infarction patient in the acute phase who has been transported to the facility. The cerebral infarction treatment support system 100 can provide the doctor or the like with support information different from a medical image, separately from the medical image (such as an X-ray image, a CT image, or an MRI image) used for diagnosis and treatment of the cerebral infarction patient in the acute stage.

The cerebral infarction treatment support system 100 includes at least a gene detection device 10, an image controller 20, and a display 30.

The detection device 10 measures a biological sample 2 collected from a patient 1 and generates first information 41 as to whether or not the biological sample 2 has a susceptibility gene for cerebral infarction. The detection device 10 is installed in an examining room of the medical facility such as a hospital, for example.

The biological sample 2 is a liquid collected from the patient 1 and containing at least the genomic DNA of the patient 1. The biological sample 2 includes a specimen such as blood or saliva collected from the patient 1, for example. The specimen includes whole blood, plasma, or serum. The sample may be a tissue or a cell of hair, nails, skin, or mucous membrane, for example. The biological sample 2 may contain a component used for measurement of the detection device 10 in addition to the specimen. The biological sample 2 may contain a lysate for eluting a gene from the specimen, a reaction solution for amplifying a gene, and the like, for example. The reaction solution is designed to specifically react with the susceptibility gene for cerebral infarction to be detected. In this description, the biological sample is a concept that includes not only the specimen itself collected from the patient 1 but also a prepared sample prepared by the specimen and other components.

The susceptibility gene for cerebral infarction significantly correlates with the likelihood of developing a particular type of cerebral infarction. That is, the presence of the susceptibility gene for cerebral infarction in the biological sample 2 indicates that the likelihood of developing a cerebral infarction of the type associated with the susceptibility gene is significantly higher or lower than that in the absence of the susceptibility gene. The susceptibility gene for cerebral infarction may be a variant of a particular gene or a genetic polymorphism. The first information 41 indicates whether such a variant of a gene or a genetic polymorphism is present or absent in the DNA in the biological sample 2.

The first information 41 is at least information with which it can be determined whether or not the susceptibility gene for cerebral infarction is present. The first information 41 may be binary information indicating either "with the susceptibility gene for cerebral infarction (positive)" or "without the susceptibility gene for cerebral infarction (negative)", for example. The first information 41 may be information indicating that there are "two variants or genetic polymorphisms, which are the susceptibility genes, (variant homozygote)", there is "one variant or genetic polymorphism, which is the susceptibility gene, (variant/wild-type heterozygote)", or there is "no variant or genetic polymorphism, which is the susceptibility gene, (wild-type homozygote)".

In the cerebral infarction treatment support system 100, second information 42 related to the diagnosis or treatment of cerebral infarction may be generated based on the first information 41 as to whether or not the susceptibility gene for cerebral infarction is present. The second information 42 may include information indicating the type of cerebral infarction that is significantly related to the susceptibility gene for cerebral infarction, for example. Furthermore, for example, a patient having the susceptibility gene may develop characteristics (traits) that facilitate development of cerebral infarction. The characteristics that facilitate development of cerebral infarction are that blood vessels in the brain tend to be thin and that blood vessel walls tend to be weak, for example. The second information 42 is secondary information generated by adding other medical and scientific findings, using the first information 41 as to whether or not the susceptibility gene for cerebral infarction is present as primary information. The second information 42 does not need to be generated by the detection device 10. The second information 42 may be generated by a computer or server capable of acquiring the first information 41 from the detection device 10 via a network, for example.

The image controller 20 acquires at least one of the first information 41 generated by the detection device 10 or the second information 42 related to the susceptibility gene generated based on the first information 41. The image controller 20 controls the display 30 to display at least one of the acquired first information 41 or second information 42. The image controller 20 includes a computer configured to be able to communicate with the detection device 10 and the display 30, for example.

Specifically, the image controller 20 includes a receiver 21 and a video output 22. The receiver 21 receives at least one of the first information 41 generated by the detection device 10 or the second information 42 related to the susceptibility gene generated based on the first information 41. The receiver 21 can directly communicate with the detection device 10 by wire or wirelessly, for example. The receiver 21 can communicate with the detection device 10 via a network, for example. The receiver 21 may not receive information from the detection device 10 as long as it can have access to a device that stores the first information 41 generated by the detection device 10 and the second information 42 generated based on the first information 41 via a network.

The video outputs 22 outputs at least one of the received first information 41 or second information 42 to the display 30. The video output 22 is electrically connected to the display 30 by wire or wirelessly. FIG. 1 shows an example in which the image controller 20 is installed outside an image interpretation room 901 and a catheter lab 902. In the example of FIG. 1, the image controller 20 delivers at least one of the first information 41 or the second information 42 to the display 30 installed in the image interpretation room 901 and the catheter lab 902.

The display 30 is a monitor that displays information. The display 30 is arranged in at least one of the catheter lab 902 in which a vascular X-ray imaging device is arranged or the image interpretation room 901 in which an image browsing terminal for radiation diagnostic images or MRI images is arranged. The image controller 20 outputs the received information (first information 41 and/or second information 42) to the display 30. The display 30 displays the information (first information 41 and/or second information 42) output from the image controller 20.

In the cerebral infarction treatment support system 100, the information (at least one of the first information 41 or the second information 42) output from the image controller 20 is displayed on the display 30 at least during the treatment or diagnosis of the patient 1.

For the cerebral infarction patient in the acute phase, a CT image or an MRI image for diagnosis is captured by a CT device or an MRI device in the hospital, and a diagnosis is made in the image interpretation room 901 of the hospital. In the cerebral infarction treatment support system 100, the information received by the image controller 20 is output to the display 30 installed in the image interpretation room 901 during the diagnosis of the patient 1, for example. The image interpretation room 901 is a room in which a radiation diagnostic device (such as an X-ray imaging device or CT device) or the image browsing terminal (PC) for diagnostic images such as an MRI is arranged.

After the diagnosis, in the stage of treatment of the cerebral infarction patient, catheter treatment is performed on an infarcted site in the cerebral blood vessel, for example. In the cerebral infarction treatment support system 100, the information received by the image controller 20 is output to the display 30 installed in the catheter lab 902 during the catheter treatment of the patient 1, for example. The catheter lab 902 is a room in which the vascular X-ray imaging device used at the time of catheter treatment is installed.

Thus, the display 30 is arranged in at least one of the catheter lab 902 or the image interpretation room 901 in the hospital. The cerebral infarction treatment support system 100 may include another display in addition to the displays 30 in the catheter lab 902 and the image interpretation room 901. Such a display 30 may be a display of a portable information terminal such as a tablet terminal carried by a doctor or the like.

Detection Device

The detection device 10 detects the susceptibility gene (gene to be detected) for cerebral infarction from the biological sample 2. To detect the susceptibility gene is to detect a specific base sequence in the genomic DNA contained in the biological sample 2. As detection results, the detection device 10 generates the first information 41 as to whether or not the biological sample 2 has the susceptibility gene for cerebral infarction.

The susceptibility gene detected by the detection device 10 is not limited to one (one type). When the presence or absence of a plurality of types of susceptibility genes for cerebral infarction significantly correlates with the likelihood of developing any type of cerebral infarction, the first information 41 may indicate the presence or absence of each of the plurality of types of susceptibility genes.

The detection device 10 amplifies the gene to be detected in the biological sample 2, for example. The detection device 10 binds the gene to be detected to a labeling substance, for example. The detection device 10 detects the susceptibility gene for cerebral infarction by detecting the labeling substance bound to the gene to be detected, for example. The labeling substance is not particularly limited as long as it is a substance that generates a signal that can be detected by the detection device 10, and includes a fluorescent substance (fluorescent label), for example. In this case, the detection device 10 irradiates the biological sample 2 with excitation light and detects fluorescence generated from the labeling substance.

Figure 2:
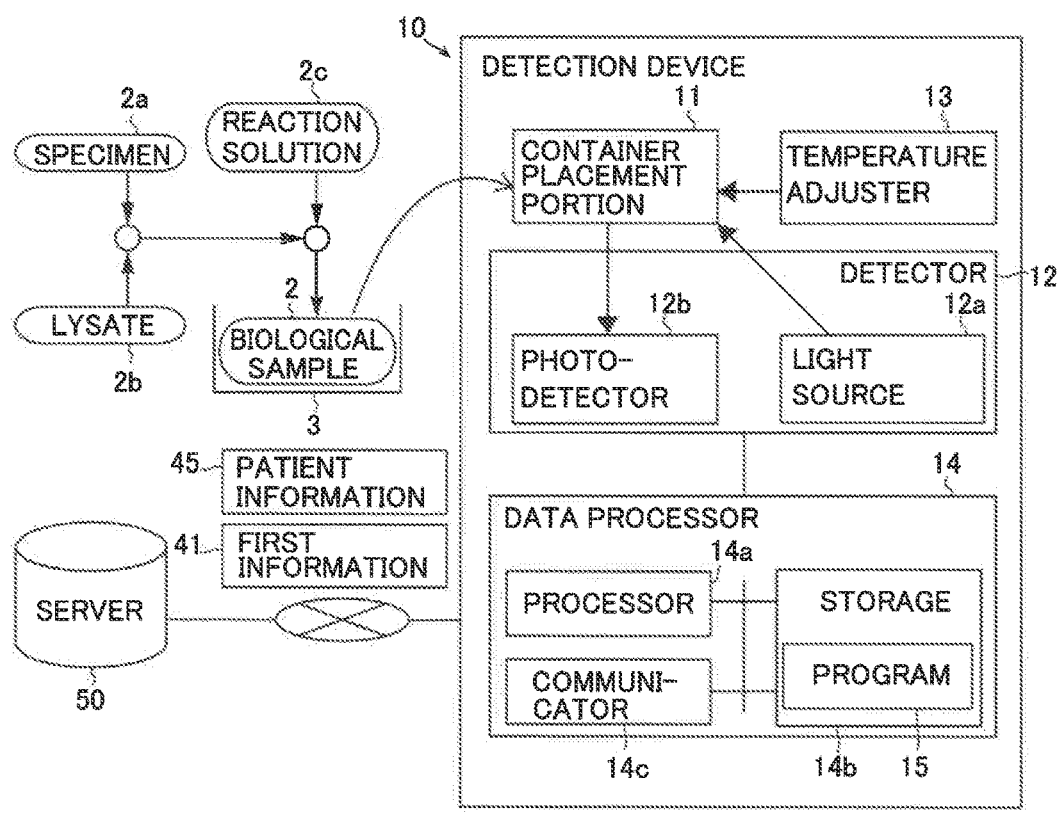
FIG. 2 is a schematic view showing a configuration example of a detection device.

In a configuration example of FIG. 2, the detection device 10 is a gene amplification detection device that amplifies a gene to be detected using a polymerase chain reaction (PCR) method and detects the gene to be detected. The detection device 10 includes a container placement portion 11, a detector 12, a temperature adjuster 13, and a data processor 14.

On the container placement portion 11, a sample container 3 containing the biological sample 2 can be installed. The sample container 3 is a translucent reaction container, and may be a so-called PCR tube or well plate, for example.

The temperature adjuster 13 heats and/or cools the sample container 3 installed on the container placement portion 11 to adjust the temperature of the biological sample 2. The temperature adjuster 13 performs a thermal cycle process to periodically raise and lower the temperature of the biological sample 2. By the thermal cycle process, the gene to be detected (susceptibility gene for cerebral infarction) in the biological sample 2 is amplified.

The detector 12 includes a light source 12a and a photodetector 12b. The light source 12a includes a light emitting diode (LED) element, for example, and generates excitation light of a fluorescent probe contained in the biological sample 2. The light source 12a irradiates the biological sample 2 in the sample container 3 installed on the container placement portion 11 with excitation light. The fluorescent probe contained in the biological sample 2 is excited by irradiation with excitation light to generate fluorescence. The photodetector 12b detects the fluorescence generated from the fluorescent probe contained in the biological sample 2. The photodetector 12b outputs a detection signal according to the fluorescence intensity generated from the biological sample 2. The photodetector 12b includes a photomultiplier tube (PMT) or a photodiode, for example.

In the configuration example of FIG. 2, the detection device 10 performs a gene amplification process on the biological sample 2 containing a specimen 2a containing blood or saliva collected from the patient 1 and a reaction solution 2c containing a component that suppresses the influence of an inhibitor in the specimen 2a. That is, the detection device 10 is a direct PCR device that performs a PCR process on the biological sample 2 prepared without performing a purification process to purify DNA from the specimen 2a. The term "direct PCR" refers to performing the PCR process without the DNA purification process. The reaction solution 2c containing the component that suppresses the influence of the inhibitor contains a PCR enzyme, a fluorescent probe, a primer, and the component that suppresses the influence of the inhibitor in the specimen 2a. As the component that suppresses the influence of the inhibitor, it is preferable to use an Ampdirect (registered trademark) buffer manufactured by Shimadzu Corporation, for example.

The detection device 10 performs a real-time PCR technique to perform a labeling process with a labeling substance in the process of gene amplification. That is, the detection device 10 specifically binds the fluorescent probe to the gene to be detected (susceptibility gene for cerebral infarction) in the gene amplification process by the PCR process, instead of performing the labeling process on an amplified product after gene amplification by the PCR process.

In the configuration example of FIG. 2, first, the specimen 2a collected from the patient 1 is mixed with a cell lysate 2b. The mixed solution of the specimen 2a and the cell lysate 2b is mixed with the reaction solution 2c in the sample container 3. The reaction solution 2c contains the PCR enzyme, the fluorescent probe, the primer, and the component that suppresses the influence of the inhibitor in the specimen 2a. Thus, the biological sample 2 is prepared. The component that suppresses the influence of the inhibitor enables the PCR process without the DNA (deoxyribonucleic acid) purification process. The detector 12 detects fluorescence indicating the presence of the gene to be detected in the process of gene amplification by a real-time PCR process, and outputs a detection signal according to the fluorescence intensity to the data processor 14.

The data processor 14 includes a computer including a processor 14a such as a central processing unit (CPU), a storage 14b that stores a program 15 for gene analysis, and a communicator 14c. The storage 14b includes a volatile and/or non-volatile storage device. The communicator 14c includes a communication interface that can be connected to a network of the medical facility such as a hospital.

The processor 14a acquires the detection signal output from the detector 12. The processor 14a analyzes the detection signal by executing the program 15 stored in the storage 14b. The processor 14a generates the first information 41 as to whether or not the biological sample 2 has the susceptibility gene for cerebral infarction by analysis. The processor 14a causes the communicator 14c to transmit the first information 41 to a server 50 via a network. The first information 41 may be directly transmitted to the image controller 20.

Patient information 45 is assigned to the biological sample 2 collected from the patient 1. The patient information 45 includes unique identification information that identifies the patient 1. For example, the detection device 10 assigns the patient information 45 of the patient 1 from which the biological sample 2 is collected to the first information 41.

FIG. 2 shows an example in which a prepared sample in which the specimen 2a, the cell lysate 2b, and the reaction solution 2c have been mixed is supplied as the biological sample 2 to the detection device 10, but instead of this, the biological sample 2 containing only the specimen 2a may be supplied to the detection device 10, for example. In this case, the detection device 10 may include a mechanism to dispense the cell lysate 2b and the reaction solution 2c into the sample container 3 containing the biological sample 2 so as to prepare a sample for measurement in the detection device 10.

The susceptibility gene for cerebral infarction may be a single nucleotide polymorphism (SNP) in the base sequence of a specific gene. Examples of a SNP detection method include a restriction fragment length polymorphism (RFLP) method, a PCR-single strand conformation polymorphism (SSCP) analysis method, an allele-specific oligonucleotide (ASO) hybridization method, a sequencing method, an amplification refracting mutation system (ARMS) method, a denaturing gradient gel electrophoresis method, an RNAseA cleavage method, a dye-labeled oligonucleotide ligation (DOL) method, a TaqMan PCR method, a primer extension method, an invader method, etc. The detection device 10 may be a device capable of implementing any of the above detection methods in addition to the configuration example shown in FIG. 2.

Susceptibility Gene for Cerebral Infarction

The susceptibility gene for cerebral infarction includes an RNF213 p.R4810K genetic polymorphism, for example.

Ring finger protein 213 (RNF213) (GenBank accession number NM_001256071.1) is present in a human chromosomal region 17q25.3.

The RNF213 p.R4810K genetic polymorphism is a single nucleotide polymorphism (SNP) of 73097 G>A in a nucleotide sequence represented by SEQ ID NO.: 2. The detection device 10 detects the SNP of 73097 G>A in the biological sample 2.

SEQ ID NO.: 2 is a partial nucleotide sequence of human chromosome 17 DNA containing the mysterin gene and genes [FLJ3520, NPTX1, CARD14, and Raptor (KIAA1303)] in the peripheral region thereof, and corresponds to the 43560001th to 43795000th nucleotide of Contig #NT010783.15 registered in NCBI.

In the nucleotide sequence represented by SEQ ID NO.: 2, in addition to the 73097th SNP, which is G or A (73097 G>A), the 4766th SNP, which is T or C (4766 T>C), the 120764th SNP, which is G or A (120764 G>A), the 152917th SNP, which is G or A (152917 G>A), and the 232102th SNP, which is G or A (232102 G>A) may be present.

In this description, the position of a SNP is described based on the position of a nucleotide in the nucleotide sequence represented by SEQ ID NO.: 2. For example, "the 73097th SNP" refers to a SNP of the 73097th nucleotide in the nucleotide sequence represented by SEQ ID NO.: 2. When described as "73097 G>A", for example, a base (G in this case) of the major allele is described before a symbol of ">", and a base (A in this case) of the minor allele is described after the symbol of ">".

In this description, a nucleotide sequence is described as a DNA sequence, unless otherwise noted. However, when a polynucleotide is ribonucleic acid (RNA), thymine (T) is appropriately replaced with uracil (U). A polynucleotide may contain any additional sequence in addition to the continuous partial sequence of the nucleotide sequence represented by SEQ ID NO.: 2 or its complementary sequence.

As a result of the investigation by the present inventors, it has been found that the RNF213 p.R4810K polymorphism increases a risk of ischemic stroke (i.e., atherothrombotic brain infarction) due to aortic atherosclerosis. The present inventors have filed patent applications based on this finding. The application numbers of the patent applications by the present inventors are Japanese Patent Application No. 2018-233549 and PCT/JP2018/045915, and this description incorporates the entire disclosure contents of these applications by reference.

FIGS. 3A to 3F show an example of the detection results of the RNF213 p.R4810K genetic polymorphism by the detection device 10. In each of graphs of FIGS. 3A to 3F, the vertical axis indicates the signal intensity (fluorescence intensity) of the detection signal of the detection device 10, and the horizontal axis indicates the number of PCR process cycles in the detection device 10.

Figure 3:
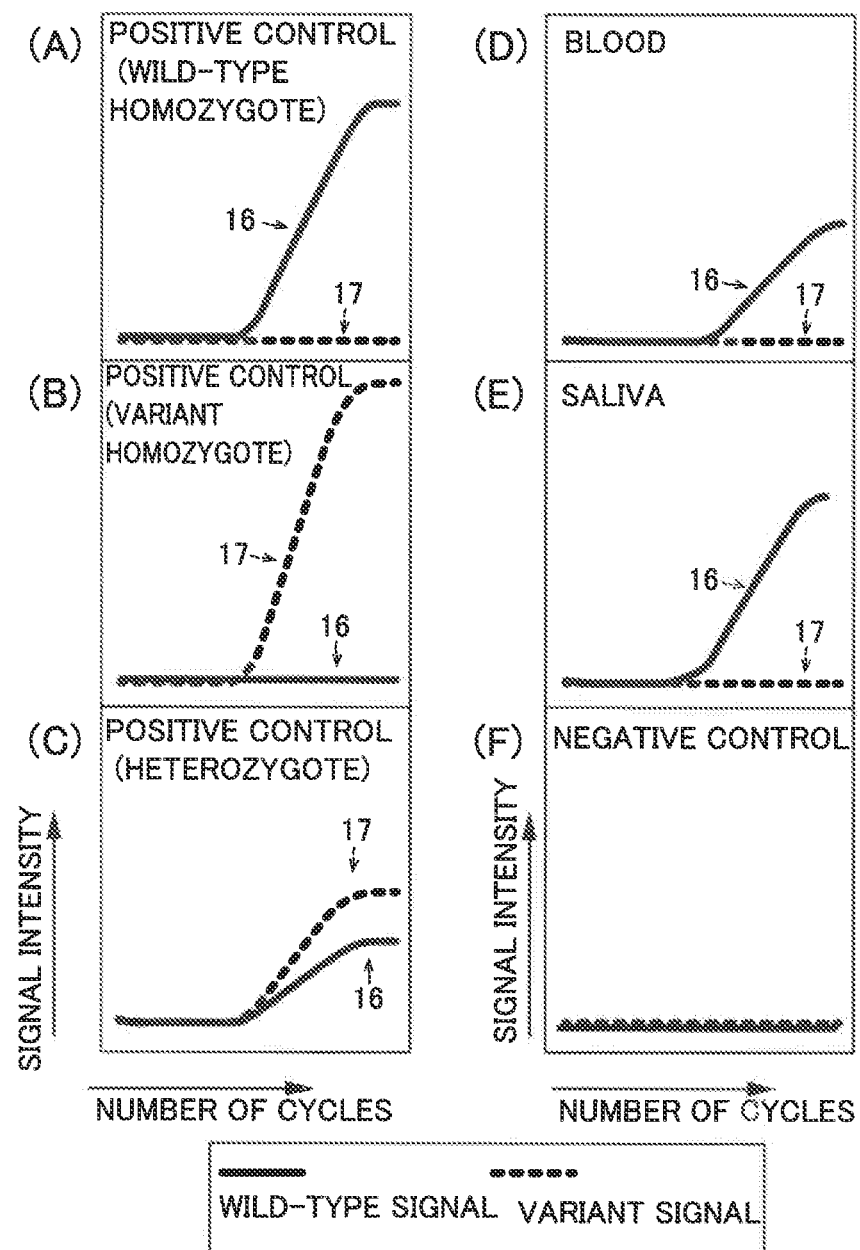
FIG. 3 includes views (A) to (F) for illustrating the detection results of the detection device.

FIG. 3 at (A) shows the detection results of the wild-type positive control of the RNF213 gene. FIG. 3 at (B) shows the detection results of the variant positive control of the RNF213 gene. The wild type refers to a base sequence in which the p.R4810K genetic polymorphism is not present, and the variant refers to a base sequence in which the p.R4810K genetic polymorphism is present. The positive control refers to a synthesis of DNA having wild-type and variant sequences. FIG. 3 at (C) shows the detection results of the positive control of a heterozygote in which one of alleles of RNF213 is wild-type and the other is variant. FIG. 3 at (D) shows the detection results using blood collected from a subject. FIG. 3 at (E) shows the detection results using saliva collected from the subject. FIG. 3 at (F) shows the detection results of the negative control for verifying the determination results of the detection device 10. The negative control refers to a sample that does not contain either a wild-type or variant form of the RNF213 gene.

In FIG. 3 at (A), the intensity of a fluorescent signal (referred to as a wild-type signal 16) generated from the fluorescent probe that specifically binds to the wild-type form of the RNF213 gene is increased, and the intensity of a fluorescent signal (referred to as a variant signal 17) generated from the fluorescent probe that specifically binds to the variant form of the RNF213 is not changed. In FIG. 3 at (B), the intensity of the wild-type signal 16 is not changed, and the intensity of the variant signal 17 is increased. In FIG. 3 at (C), the intensities of both the wild-type signal 16 and the variant signal 17 are increased. Therefore, from the detection results of the detection device 10, the presence or absence of the RNF213 p.R4810K genetic polymorphism can be determined based on the intensity change of the variant signal 17.

From FIGS. 3 at (D) and (E) FIGS. 3D and 3E, it has been confirmed that changes in signal intensity similar to those for the positive control can be obtained from blood and saliva specimens actually collected from the subject. From FIG. 3 at (F) FIG. 3F, it has been confirmed that there was no non-specific amplification and that specific amplification and labeling for the gene to be detected are achieved.

From the above, the data processor 14 shown in FIG. 2 determines the presence or absence of the susceptibility gene (RNF213 p.R4810K genetic polymorphism) for cerebral infarction based on the intensity change of the variant signal 17. The data processor 14 creates the first information 41 according to the determination results. That is, the data processor 14 generates the first information 41 indicating that the susceptibility gene for cerebral infarction is present when the intensity of the signal (variant signal 17) derived from the labeling substance for the susceptibility gene for cerebral infarction is increased in the detection results. The data processor 14 generates the first information 41 indicating that the susceptibility gene for cerebral infarction is not present when the intensity of the signal (variant signal 17) derived from the labeling substance for the susceptibility gene for cerebral infarction is not increased in the detection results.

For example, a threshold is set for the signal intensity as a criterion for determining the presence or absence of the susceptibility gene in the detection results. The data processor 14 acquires a difference value between the signal intensity at the start of the PCR process and the signal intensity at the end of the PCR process, and determines that the susceptibility gene is present when the acquired difference value exceeds the threshold, for example. Simply, when the signal intensity of the variant signal 17 exceeds the threshold, it may be determined that the susceptibility gene is present.

The susceptibility gene for cerebral infarction may be other than the RNF213 p.R4810K genetic polymorphism. Recent genetic studies suggest a correlation between cardiogenic cerebral infarction and both PITX2 (human chromosomal region 4q25) and ZFHX3 (human chromosomal region 16q22) as related genes. Furthermore, recent genetic studies suggest a correlation between lacunar infarction and ALDH2 (human chromosomal region 12q24), for example, as a related gene. The susceptibility gene for cerebral infarction may include one or more of these genes. The susceptibility gene for cerebral infarction is not limited to the above as long as it is a gene that shows a significant correlation with a specific cerebral infarction.

Second Information

The second information 42 is now described. In an example shown in FIG. 4, the second information 42 includes at least one of information 42a about the type of cerebral infarction, information 42b about the cerebral blood vessel of the patient 1, or information 42c indicating a treatment device recommended or deprecated for use in catheter treatment of the cerebral infarction of the patient 1 (hereinafter referred to as "device information 42c"). The second information 42 is generated in the form of a message (sentence) to a user, for example.

The information 42a about the type of cerebral infarction is information indicating the type of cerebral infarction that significantly correlates with the susceptibility gene, the presence or absence of which has been detected with the first information 41. The types of cerebral infarction are classified into three types: cardiogenic cerebral embolism, lacunar infarction, and atherothrombotic cerebral infarction. The presence of the susceptibility gene indicates that the likelihood of developing any type of cerebral infarction is significantly higher or lower, for example. The information 42a about the type of cerebral infarction may be a message indicating the type of cerebral infarction that is significantly more or less likely to be developed.

The information 42b about the cerebral blood vessel of the patient 1 is information on the morphology or nature of the cerebral blood vessel of the patient 1 inferred based on the presence or absence of the susceptibility gene. The information 42b about the cerebral blood vessel of the patient 1 may be a message indicating that the cerebral blood vessel tends to be thick or thin, for example, when the susceptibility gene is present. The information 42b about the cerebral blood vessel of the patient 1 may be a message indicating that the cerebral blood vessel tends to be strong (hard to be damaged) or weak (vulnerable), for example, when the susceptibility gene is present.

The device information 42c is information indicating the type or shape of a treatment device that is an option in catheter treatment.

Figure 5:
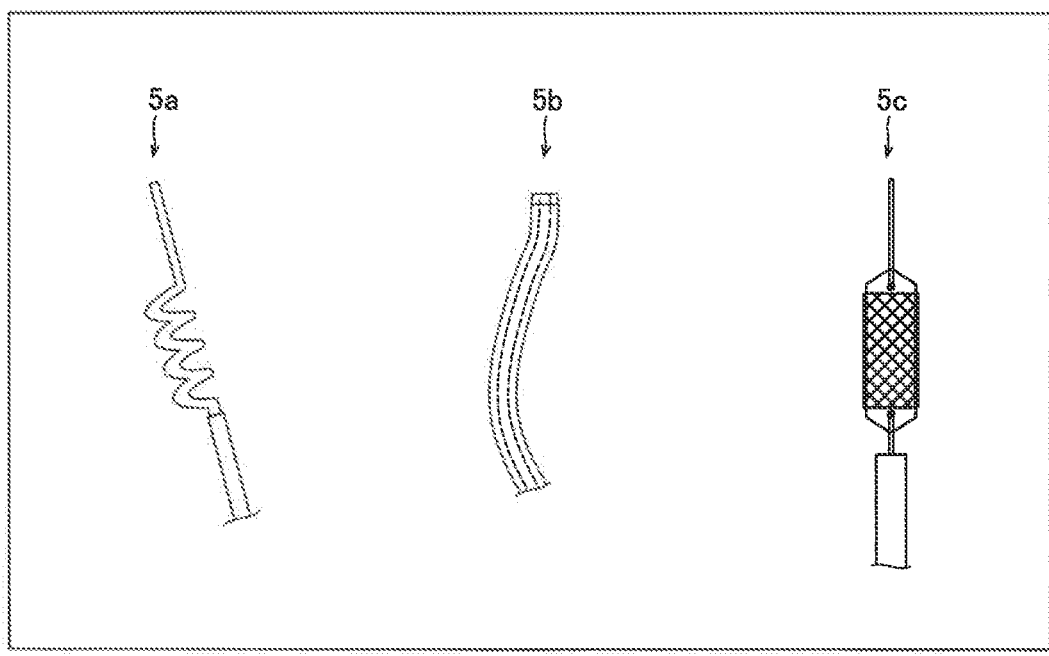
FIG. 5 is a schematic view showing the types of treatment devices.

Treatment devices for catheter treatment of cerebral infarction include a thrombus retrieval device 5a, a thrombus suction device 5b, a percutaneous angioplasty device 5c shown in FIG. 5, etc. The thrombus retrieval device 5a includes a coiled wire for entwining and retrieving the thrombus. The thrombus suction device 5b has a hollow tubular shape, and can remove the thrombus by suctioning the thrombus thereinto. The percutaneous angioplasty device 5c includes a balloon catheter and a stent.

The device information 42c may be a message indicating a treatment device recommended or deprecated for use among the thrombus retrieval device 5a, the thrombus suction device 5b, and the percutaneous angioplasty device 5c, for example.

For example, when the RNF213 p.R4810K genetic polymorphism is present, the likelihood of developing atherothrombotic cerebral infarction significantly increases. Furthermore, when this genetic polymorphism is present, a relatively thick blood vessel in the brain, which is an infarcted site due to atherothrombotic cerebral infarction, tends to be thinner than the same site in a group not having this genetic polymorphism. Moreover, the relatively thick blood vessel in the brain tends to be thinner than normal, and thus the use of the thrombus retrieval device that is prone to contact a blood vessel may lead to reocclusion due to endothelial damage to the occluded blood vessel.

Therefore, as an example, when the first information 41 indicates the presence of the RNF213 p.R4810K genetic polymorphism, as shown in FIG. 6, the information 42a about the type of cerebral infarction includes a message indicating that the type of cerebral infarction developed by the patient 1 from which the biological sample 2 has been collected is "more likely to be atherothrombotic cerebral infarction". The information 42b about the cerebral blood vessel of the patient 1 includes a message indicating that regarding the patient 1 from which the biological sample 2 has been collected, "the cerebral blood vessel tends to be thin". The device information 42c includes a message indicating that "the use of the thrombus retrieval device 5a is deprecated" and/or "the use of the thrombus suction device 5b or the percutaneous angioplasty device 5c is recommended". The device information 42c may include a message indicating that "the use of a treatment device having a smaller diameter than usual is recommended".

Figure 4:
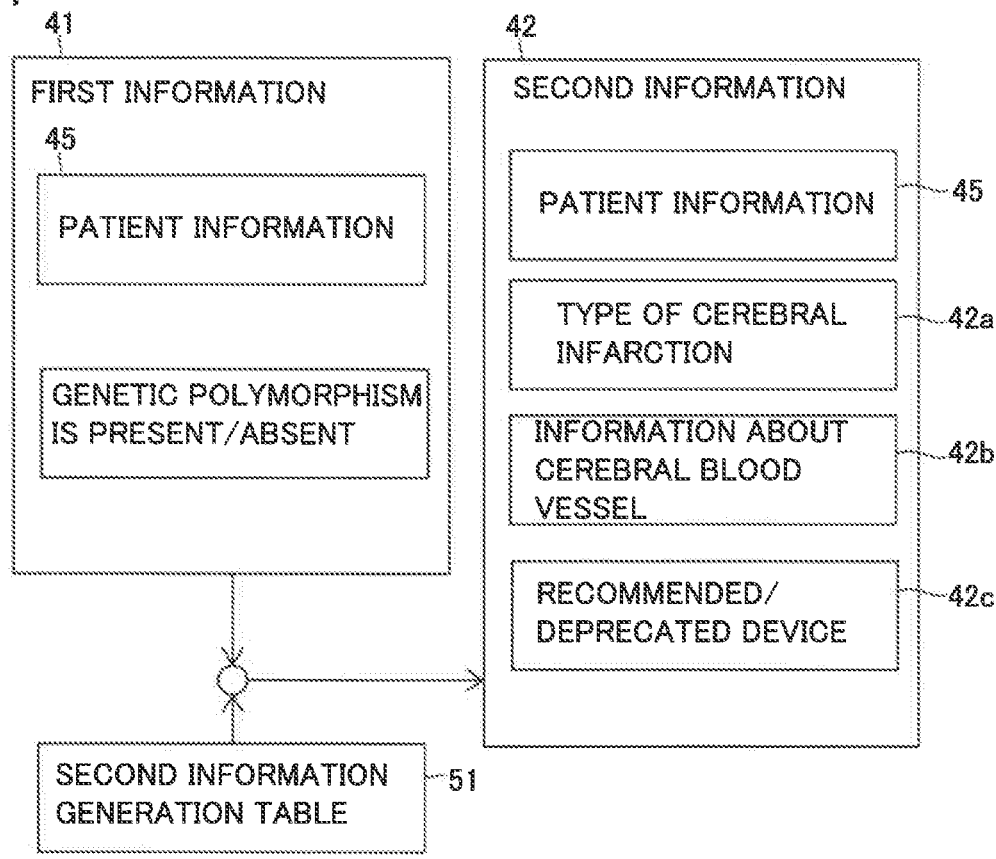
FIG. 4 is a diagram for illustrating second information.

In the configuration example of FIG. 2, the cerebral infarction treatment support system 100 includes the server 50 that is communicably connected to the detection device 10 and the image controller 20 and stores the first information 41. As shown in FIG. 4, the server 50 generates the second information 42 based on the first information 41.

As described above, the server 50 includes a second information generation table 51 for generating the second information 42 according to the contents (the susceptibility gene is present/absent) of the first information 41. The second information generation table 51 is a data table in which the presence or absence of a specific susceptibility gene and the contents of the second information 42 to be generated corresponding to the presence or absence of the susceptibility gene are recorded in association with each other. When acquiring the first information 41 from the detection device 10, the server 50 generates the second information 42 by referring to the second information 42 corresponding to the contents of the first information 41 from the second information generation table 51. The second information 42 is associated with the first information 41 or the patient information 45 assigned to the first information 41. The patient information 45 assigned to the first information 41 may also be assigned to the second information 42.

The second information 42 may be generated by the server 50 in a hospital, or may be generated by a cloud server or the like via the Internet. The detection device 10 may generate the second information 42 together with the first information 41. The server 50 includes at least one of a radiology information system server or a medical image management system server, each of which is connected to an in-hospital network, for example. The radiology information system server is called an RIS (radiology information system) server 52 (see FIG. 7), and is a server that performs the processing of a system that mainly performs examination with radiology devices and manages the examination results. The medical image management system server is a server that collects and records medical image data, and is also called a DICOM server 53 (see FIG. 7) because it handles medical image data conforming to the DICOM standard, which is a standard.

The image controller 20 (see FIG. 1) receives at least the second information 42 from the server 50, for example. The image controller 20 outputs at least the received second information 42 to the display 30 and causes the display 30 to display it. The image controller 20 may receive both the first information 41 and the second information 42 and cause the display 30 to display them. The image controller 20 may cause the display 30 to display only the first information 41, and in this case, the cerebral infarction treatment support system 100 may not generate the second information 42.

Configuration Example of Cerebral Infarction Treatment Support System

FIG. 7 shows a more specific configuration example of the cerebral infarction treatment support system 100. The cerebral infarction treatment support system 100 may be configured as a portion or all of an in-hospital network.

The radiology devices such as a CT device 101 and an MRI device 102 and the detection device 10 are connected to the in-hospital network. Various portable terminals 103 such as a tablet-type information terminal and various servers such as the RIS server 52 and the DICOM server 53 are connected to the in-hospital network. Furthermore, a vascular X-ray imaging device 70 installed in the catheter lab 902 and an image browsing terminal 80 installed in the image interpretation room 901 are connected to the in-hospital network.

The vascular X-ray imaging device 70, a catheter device 104, and the like are installed in the catheter lab 902. At the time of treatment, a treatment device 5 to be used is prepared. The vascular X-ray imaging device 70 is a vascular imaging device that performs fluoroscopic imaging of blood vessels. The vascular X-ray imaging device 70 detects X-rays emitted from an X-ray source with an X-ray detector and images the X-rays. The vascular X-ray imaging device 70 includes a first control device 71 that performs a process to control a device, and a first display 72 that displays a captured X-ray image. The vascular X-ray imaging device 70 performs fluoroscopic imaging of the catheter and the treatment device 5 introduced into the blood vessel at the time of catheter treatment in a moving image format, and displays them on the first display 72. The details of the vascular X-ray imaging device 70 are described below.

The image browsing terminal 80 installed in the image interpretation room 901 is a personal computer (PC), for example, and includes a second control device 81 constituting a PC main body and a second display 82. In the image interpretation room 901, a doctor or the like browses a medical image of the patient 1 using the image browsing terminal 80, identifies and diagnoses a thrombus site of the cerebral infarction patient 1, and determines courses of treatment, for example. The medical image includes a CT image captured by the CT device 101 and an MRI image captured by the MRI device.

In the configuration example of FIG. 7, the image controller 20 includes the first control device 71 of the vascular X-ray imaging device 70 installed in the catheter lab 902. The first control device 71 includes the receiver 21 and the video output 22. The display 30 includes the first display 72 installed in the catheter lab 902 and configured to display an X-ray image 73 captured by the vascular X-ray imaging device 70.

Specifically, the first control device 71 outputs at least one of the received first information 41 or second information 42, and the X-ray image 73 of the patient 1 captured by the vascular X-ray imaging device 70 to the first display 72 during catheter treatment of the patient 1 in the catheter lab 902. Consequently, the information (at least one of the first information 41 or the second information 42) received by the image controller 20 is displayed during the treatment of the patient 1 in the catheter lab 902.

In the configuration example of FIG. 7, the image controller 20 includes the second control device 81 of the image browsing terminal 80 installed in the image interpretation room 901. The second control device 81 includes the receiver 21 and the video output 22. The display 30 includes the second display 82 installed in the image interpretation room 901 and configured to display a screen of the image browsing terminal 80.

Specifically, the second control device 81 receives at least one of the first information 41 or the second information 42, and a CT image 6 or MRI image 7 of the patient 1, and outputs them to the second display 82 during diagnosis of the patient 1 in the image interpretation room 901. Consequently, the information (at least one of the first information 41 or the second information 42) received by the image controller 20 is displayed during diagnosis of the patient 1 in the image interpretation room 901.

As described above, the first information 41 and the second information 42 are recorded in the server 50 (RIS server 52 or DICOM server 53) while the patient information 45 is assigned to the first information 41 and the second information 42, or the first information 41 and the second information 42 are associated with the patient information 45. Furthermore, the patient information 45 is assigned to the X-ray image 73 captured by the vascular X-ray imaging device 70, the CT image 6, and the MRI image 7 at the time of imaging. It can be identified that these images, the first information 41, and the second information 42 have been acquired from the same patient 1 based on the patient information 45.

Therefore, in the above configuration example, the image controller 20 receives the images of the patient 1 to which the patient information 45 has been assigned, and outputs the images having the same patient information 45, and at least one of the first information 41 or the second information 42 to the display 30. The images of the patient 1 include any one of the X-ray image 73 captured by the vascular X-ray imaging device 70, the CT image 6, and the MRI image 7, and may include a medical image other than these.

The cerebral infarction treatment support system 100 may provide a doctor or the like with at least one of the first information 41 or the second information 42 at the time of postoperative evaluation and confirmation of the progress of treatment after the treatment of the cerebral infarction patient 1.

Flow of Treatment of Patient

Figure 8:
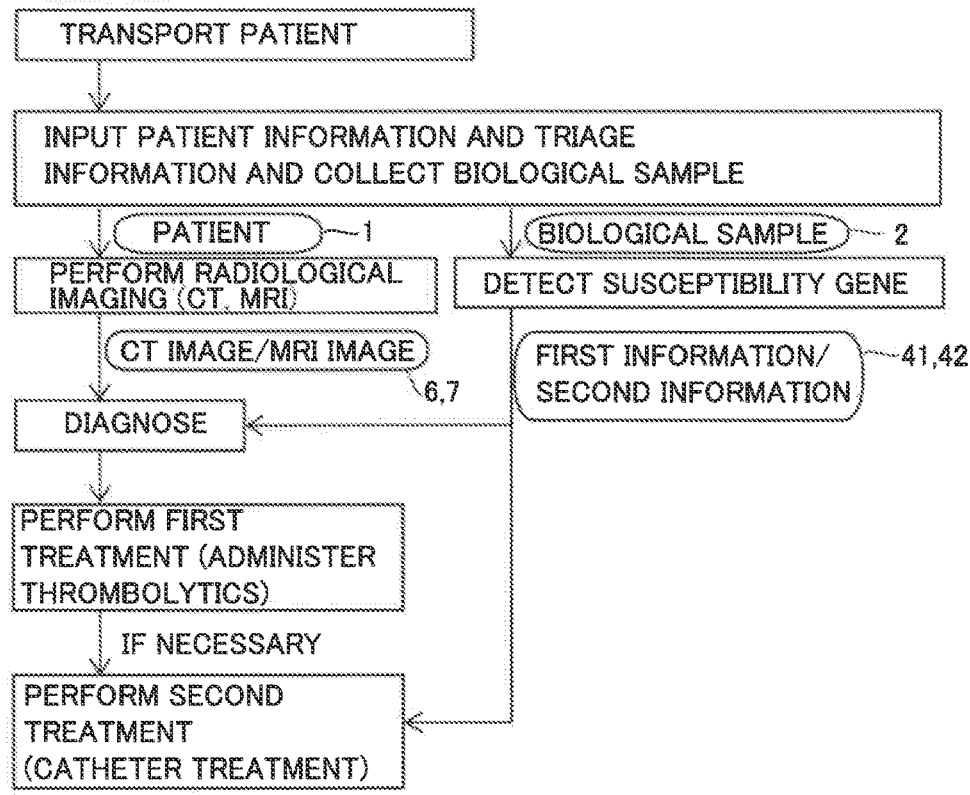
FIG. 8 is a flowchart for illustrating the flow of treatment of cerebral infarction patients in the acute phase.

The flow of the treatment of the cerebral infarction patient 1 in the acute phase is now briefly described with reference to FIG. 8.

First, the patient 1 who is presumed to have developed cerebral infarction is transported into a hospital as an emergency.

After the transportation, the patient information 45 and triage information are input to an in-hospital network system. The triage information is information indicating the priority of the treatment sequence determined based on the severity of the patient 1. Furthermore, the specimen 2a is acquired from the patient 1.

For the patient 1, the CT image 6 or the MRI image 7 is captured by the CT device 101 or the MRI device 102 in an imaging room. The biological sample 2 is prepared from the specimen 2a and supplied to the detection device 10 concurrently with the imaging of the patient 1. The cerebral infarction treatment support system 100 detects the susceptibility gene with the detection device 10 concurrently with the imaging of the patient 1.

Then, in the image interpretation room 901, the patient 1 is diagnosed based on the captured CT image 6 or MRI image 7. The image controller 20 displays at least one of the first information 41 or the second information 42 together with the images of the patient 1 based on the patient information 45 (see FIG. 6). Based on the provided information, a doctor or the like diagnoses that the patient 1 has developed cerebral infarction, identifies a thrombus site, and determines courses of treatment.

For example, a first treatment is performed according to the courses of the treatment. The first treatment is to administer thrombolytics to the patient 1. When the administration of the thrombolytics does not sufficiently improve the blood flow of the cerebral blood vessel, for example, a second treatment is performed as necessary. The second treatment is catheter treatment.

During the catheter treatment, the image controller 20 displays at least one of the first information 41 or the second information 42 together with the X-ray image 73 (see FIG. 7) of the patient 1 based on the patient information 45. The doctor in charge of treatment selects the treatment device 5, referring to the provided information, and performs the catheter treatment, referring to the intravascular X-ray image 73.

Operation of Cerebral Infarction Treatment Support System

Figure 9:
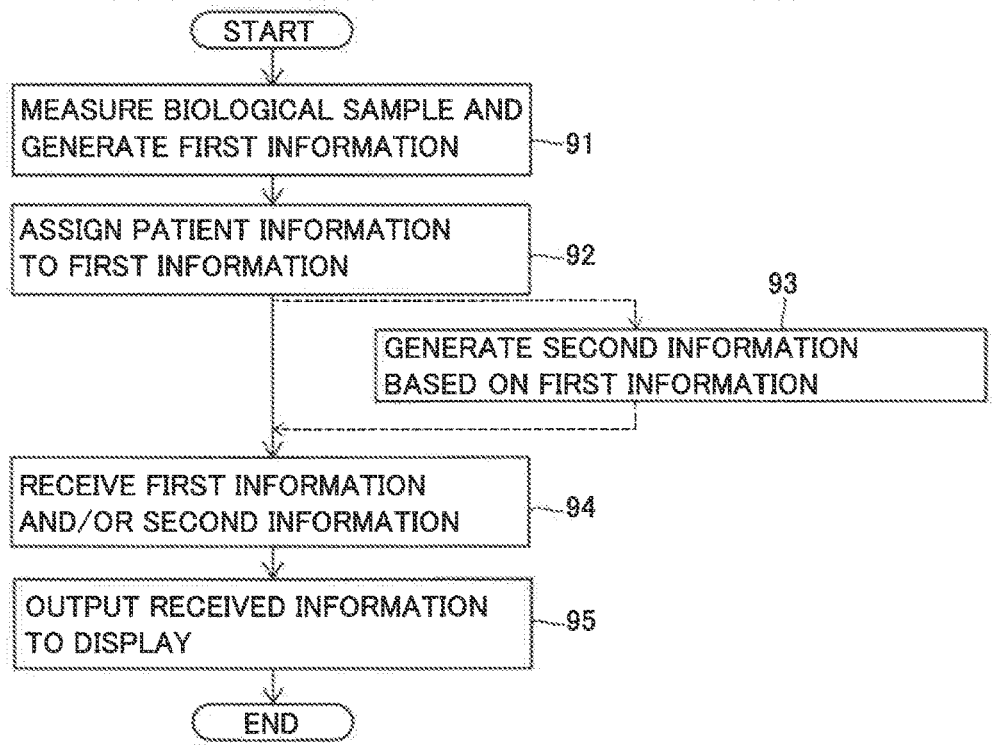
FIG. 9 is a flowchart showing a cerebral infarction treatment support method.

The operation of the cerebral infarction treatment support system 100 is now described with reference to FIG. 9. The cerebral infarction treatment support system 100 implements a cerebral infarction treatment support method according to this embodiment. For the detection device 10, refer to FIG. 2, and for the first information 41, the second information 42, and the patient information 45, refer to FIGS. 4 and 6.

In step 91, the detection device 10 measures the biological sample 2 collected from the patient 1 and generates the first information 41 as to whether or not the biological sample 2 has the susceptibility gene for cerebral infarction.

In step 92, the detection device 10 assigns the patient information 45 of the patient 1 to the first information 41 generated by the biological sample 2 collected from the patient 1 transported as an emergency.

In step 93, the second information 42 may be generated based on the first information 41. When the second information 42 is not displayed, step 93 is unnecessary.

In step 94, the receiver 21 (see FIGS. 1 and 7) of the image controller 20 receives at least one of the first information 41 or the second information 42.

In step 95, the video output 22 (see FIGS. 1 and 7) of the image controller 20 outputs at least one of the first information 41 or the second information 42 received by the image controller 20 to the display 30 and causes the display 30 to display it. The image controller 20 receives the first information 41 of the patient 1 from which the biological sample 2 has been collected based on the patient information 45, and outputs the first information 41 to the display 30 (see FIGS. 1 and 7).

The first information 41 and/or the second information 42 may be displayed only during treatment or during diagnosis of the patient 1. In particular, the treatment of the cerebral infarction patient 1 in the acute phase needs to be carried out in a short period of time. Therefore, when it takes time to detect the susceptibility gene, it is conceivable that generation of the first information 41 has not been completed during the diagnosis of the patient 1. Even in that case, in this embodiment, the received information is displayed together with the patient information 45 on the display 30 by at least the time of treatment of the patient 1. A doctor who performs the treatment can select the treatment device 5, referring to the first information 41 and/or the second information 42.

Another Configuration Example of Cerebral Infarction Support System

A cerebral infarction treatment support system 200 according to another configuration example is now described with reference to FIGS. 10 and 11. The cerebral infarction treatment support system 200 implements a cerebral infarction treatment support method according to this embodiment.

Figure 10:
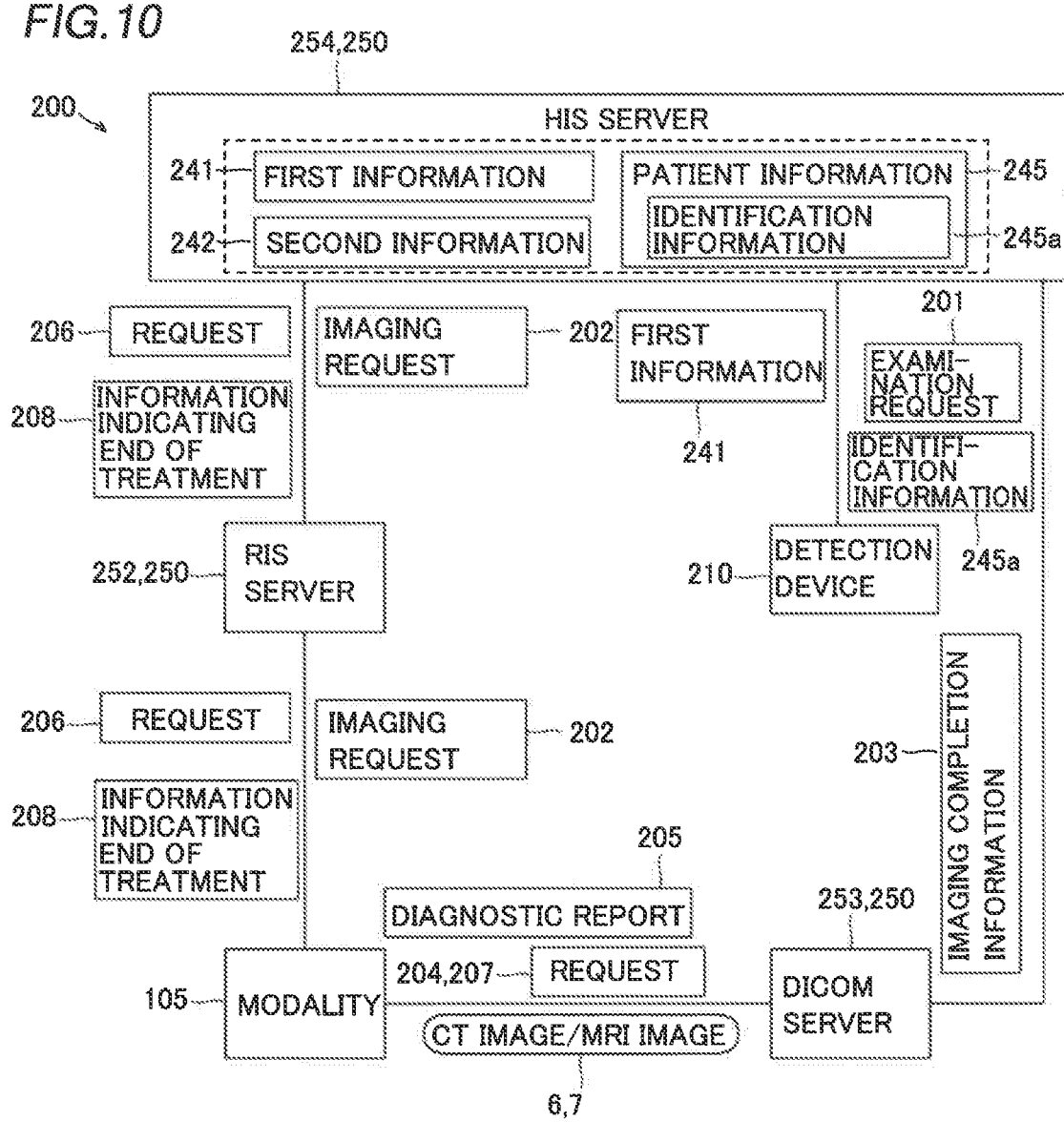
FIG. 10 is a schematic view for illustrating the linkage of information between each server and a modality in the cerebral infarction treatment support system.

In a configuration example shown in FIG. 10, the cerebral infarction treatment support system 200 includes a detection device 210, a server 250, and a modality 105. The server 250 is an example of a "manager" in the claims.

The server 250 includes a RIS server 252, a DICOM server 253, and a hospital information system server connected to an in-hospital network. The hospital information system server is called an HIS (hospital information system) server 254, and includes an automatic reception system, an electronic medical record management system, a medical accounting system, a medical treatment reservation system, a pharmacy management system, etc., for example. The HIS server 254 stores patient information 245. The RIS server 252 and the DICOM server 253 have the same or similar configurations as the RIS server 52 (see FIG. 7) and the DICOM server 53 (see FIG. 7), respectively, and thus detailed description thereof is omitted.

The modality 105 includes a vascular X-ray imaging device 270 (see FIG. 11), an image browsing terminal 80 (see FIG. 11), a CT device 101 (see FIG. 7), an MRI device 102 (see FIG. 7), etc. In this description, the "modality" refers to a generic term for these medical imaging devices. The vascular X-ray imaging device 270 has the same or similar configuration as the vascular X-ray imaging device 70, and thus detailed description thereof is omitted. The vascular X-ray imaging device 270 is an example of a "device used to treat a patient" in the claims.

Gene-Related Information

The detection device 210 measures a biological sample 2 collected from a patient 1 and generates gene-related information 240 related to a susceptibility gene for cerebral infarction. The gene-related information 240 includes first information 241 as to whether or not the biological sample 2 has the susceptibility gene for cerebral infarction, and second information 242 related to the susceptibility gene generated based on the first information 241.

First Information and Second Information

The server 250 generates the second information 242 related to the susceptibility gene based on the first information 241 included in the gene-related information 240 generated by the detection device 210. The first information 241 is the same or similar information as the first information 41 (see FIG. 4). That is, the first information 241 includes the patient information 245 and information as to whether or not a genetic polymorphism is present. The patient information 245 is the same or similar information as the patient information 45 (see FIG. 4), and includes identification information 245a. The identification information 245a is unique information that can identify the patient 1. The identification information 245a includes a patient identification number, for example. The second information 242 is the same or similar information as the second information 42 (see FIG. 4). That is, the second information 242 includes at least one of information 42a about the type of cerebral infarction, information 42b about the cerebral blood vessel of the patient 1, and information 42c indicating a treatment device recommended or deprecated for use in catheter treatment of the cerebral infarction of the patient 1.

In the example shown in FIG. 10, the HIS server 254 transmits an examination request 201 to the detection device 210. When transmitting the examination request 201, the HIS server 254 also transmits the identification information 245a of the patient 1 to be examined.

The detection device 210 that has received the examination request 201 performs the examination and generates the first information 241. Furthermore, the detection device 210 associates the generated first information 241 with the identification information 245a transmitted together with the examination request 201. The detection device 210 transmits the first information 241 associated with the identification information 245a to the HIS server 254.

The HIS server 254 manages the first information 241 transmitted from the detection device 210. Note that managing the first information 241 includes storing the first information 241 in the HIS server 254. Furthermore, managing the first information 241 includes transmitting the first information 241 to the vascular X-ray imaging device 270 and the like.

The server 250 generates the second information 242 related to the susceptibility gene based on the first information 241 included in the gene-related information 240 generated by the detection device 210.

In this embodiment, the server 250 stores the identification information 245a of the patient 1. Furthermore, the server 250 is communicably connected to the detection device 210. Moreover, the server 250 manages the set identification information 245a of the patient 1 and the stored identification information 245a of the patient 1 in association with each other, and manages at least one of the stored identification information 245a of the patient 1 or the patient information 245 of the patient 1 according to the identification information 245a of the patient 1, and the gene-related information 240 in association with each other. In this embodiment, a process to set the identification information 245a of the patient 1 in the gene-related information 240 is executed by the detection device 210 that generates the gene-related information 240.

In this embodiment, the server 250 associates at least one of the first information 241 or the second information 242 with the identification information 245a that identifies the patient 1 (see FIG. 1) to manage at least one of the first information 241 or the second information 242 and the patient information 245 of the patient 1 in association with each other. In this embodiment, the HIS server 254 associates the second information 242 with the patient information 245. Furthermore, the HIS server 254 stores the second information 242 in association with the patient information 245.

The HIS server 254 transmits an imaging request 202 for the patient 1 to the RIS server 252. The RIS server 252 transmits the imaging request 202 to the modality 105 based on the received imaging request 202. Specifically, when a request for acquiring a CT image 6 of the patient 1 is transmitted, the RIS server 252 transmits the imaging request 202 to the CT device 101. When a request for acquiring an MRI image 7 of the patient 1 is transmitted, the RIS server 252 transmits the imaging request 202 to the MRI device 102. The imaging request 202 may include the patient information 245.

The modality 105 (here, the CT device 101 or the MRI device 102) that has received the imaging request 202 images the patient 1. After the imaging is completed, the modality 105 transmits the acquired image (CT image 6 or MRI image 7) to the DICOM server 253.

The DICOM server 253 stores the transmitted image (CT image 6 or MRI image 7). The patient information 245 included in the imaging request 202 is associated with the patient information 245 stored in the HIS server 254 such that at least one of the first information 241 or the second information 242 stored in the HIS server 254 and the patient information 245 can be stored in a header of the transmitted image. Furthermore, the DICOM server 253 transmits imaging completion information 203 indicating that capturing of the image (CT image 6 or MRI image 7) has been completed to the HIS server 254.

The HIS server 254 that has received the imaging completion information 203 stores completion of the imaging in the transmitted imaging request 202.

The modality 105 acquires the first information 241, the second information 242, and the image (CT image 6 or MRI image 7) by transmitting requests (requests 204, 206, and 207) to the server 250.

Specifically, when diagnosis of cerebral infarction is performed, the image browsing terminal 80 acquires the image (CT image 6 or MRI image 7) from the DICOM server 253 by being operated by a doctor or the like. The image browsing terminal 80 transmits an image transmission request 204 to the DICOM server 253 by being operated by the doctor or the like. The DICOM server 253 that has received the image transmission request 204 transmits the image (CT image 6 or MRI image 7) to the image browsing terminal 80. For example, the doctor or the like creates a diagnostic report 205 regarding a stenosis site or the like based on the image (CT image 6 or MRI image 7) transmitted to the image browsing terminal 80. The created diagnostic report 205 is transmitted to the DICOM server 253, for example. The DICOM server 253 stores the transmitted diagnostic report 205.

The vascular X-ray imaging device 270 transmits the requests 206 and 207 to the server 250 to acquire at least one of the first information 241 or the second information 242 and the image (CT image 6 or MRI image 7) when treatment of cerebral infarction is performed. The vascular X-ray imaging device 270 acquires the information and the image transmitted from the server 250 in response to the requests 206 and 207.

A configuration in which the server 250 transmits at least one of the first information 241 or the second information 242 and the image (CT image 6 or MRI image 7) to the vascular X-ray imaging device 270 is now described with reference to FIG. 11.

Figure 11:
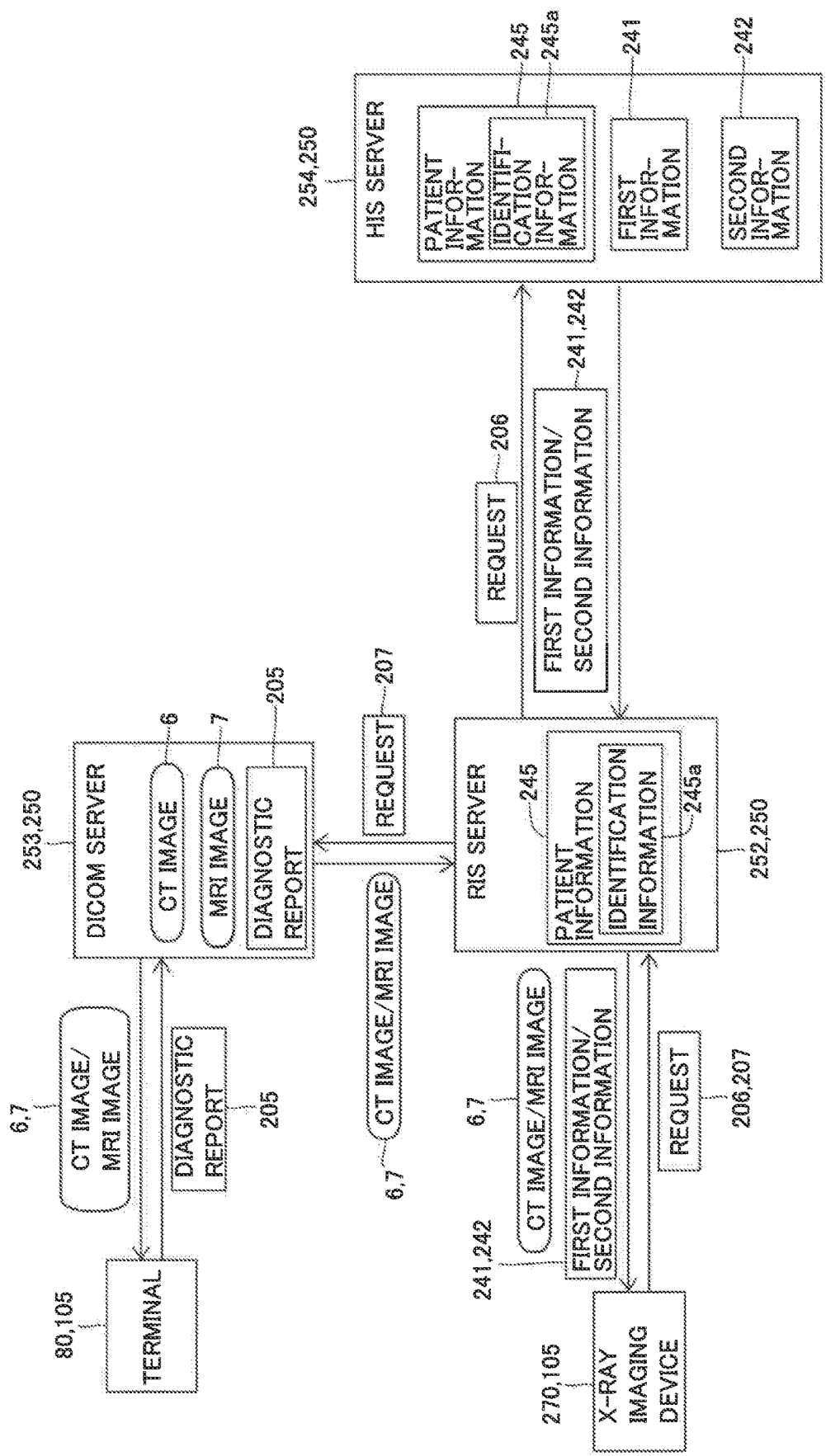
FIG. 11 is a schematic view for illustrating a process to transmit the first information and/or the second information to an X-ray imaging device.

As shown in FIG. 11, the vascular X-ray imaging device 270 transmits, to the RIS server 252, the request 206 for acquiring at least one of the first information 241 or the second information 242 by being operated by the doctor or the like. The vascular X-ray imaging device 270 also transmits the identification information 245*a* when transmitting the transmission request 206.

The RIS server 252 that has received the request 206 transmits the request 206 and the identification information 245*a* to the HIS server 254.

The HIS server 254 that has received the request 206 transmits at least one of the first information 241 or the second information 242 associated with the identification information 245*a* to the RIS server 252 based on the received identification information 245*a*.

The RIS server 252 transmits at least one of the received first information 241 or second information 242 to the vascular X-ray imaging device 270.

The vascular X-ray imaging device 270 transmits the transmission request 207 for the image (CT image 6 or MRI image 7) to the DICOM server 253 based on an operation by the doctor or the like. The vascular X-ray imaging device 270 also transmits the identification information 245*a* when transmitting the transmission request 207.

The DICOM server 253 that has received the transmission request 207 identifies the image (CT image 6 or MRI image 7) of the patient 1 from a plurality of stored images (CT images 6 or MRI images 7) based on the identification information 245*a*. The DICOM server 253 transmits the identified image (CT image 6 or MRI image 7) to the vascular X-ray imaging device 270 via the RIS server 252.

That is, the server 250 associates the second information 242 with the CT image 6 or MRI image 7 of the patient 1, using the identification information 245*a*. Furthermore, the server 250 transmits at least one of the first information 241 or the second information 242 to the vascular X-ray imaging device 270. In this embodiment, the server 250 transmits the CT image 6 or MRI image 7 of the patient 1 and the second information 242 to the vascular X-ray imaging device 270 based on the request 206 and the request 207 from the vascular X-ray imaging device 270.

In this embodiment, a configuration in which the RIS server 252 transmits at least one of the first information 241 or the second information 242 to the vascular X-ray imaging device 270 is adopted, but when at least one of the first information 241 or the second information 242 is stored in the CT image 6 or MRI image 7 itself of the patient 1 stored in the DICOM server 253, it is not necessary for the RIS server 252 to transmit at least one of the first information 241 or the second information 242. In this case, at least one of the first information 241 or the second information 242 may be stored in the header of the CT image 6 or MRI image 7 of the patient 1.

Process to Transmit First Information and/or Second Information

Figure 12:
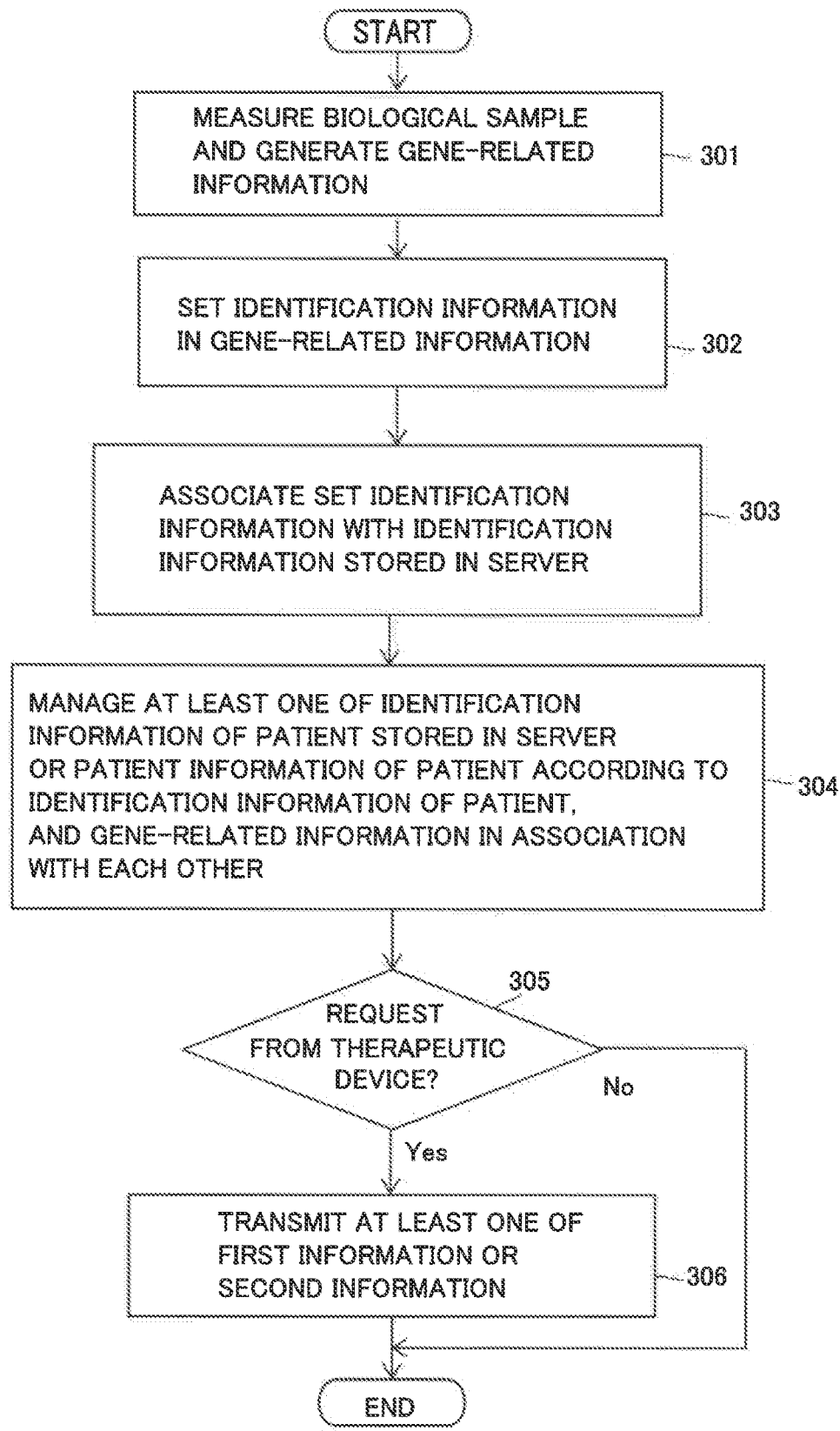
FIG. 12 is a flowchart showing a process to transmit the first information and/or the second information.

A process of the server 250 to generate the first information 241 and the second information 242 is now described with reference to FIG. 12.

In step 301, the detection device 210 measures the biological sample 2 collected from the patient 1 and generates the gene-related information 240 related to the susceptibility gene for cerebral infarction. The detection device 210 transmits the generated gene-related information 240 to the server 250.

In step 302, the detection device 210 sets the identification information 245*a* of the patient 1 in the gene-related information 240.

In step 303, the server 250 associates the set identification information 245*a* of the patient 1 with the identification information 245*a* of the patient stored in the server 250.

In step 304, the server 250 manages at least one of the identification information 245*a* of the patient 1 stored in the server 250 or the patient information 245 of the patient 1 according to the identification information 245*a* of the patient 1, and the gene-related information 240 in association with each other. The gene-related information 240 includes the first information 241 as to whether or not the biological sample 2 has the susceptibility gene for cerebral infarction, and the second information 242 related to the susceptibility gene generated based on the first information 241. In this embodiment, the server 250 manages at least one of the identification information 245*a* of the patient 1 stored in the server 250 or the patient information 245 of the patient 1 according to the identification information 245*a* of the patient 1, and at least one of the first information 241 or the second information 242 in association with each other. Specifically, the server 250 manages the second information 242 and the patient information 245 in association with each other.

In step 305, the server 250 determines whether or not there is the request 206 for transmitting the first information 241 and/or the second information 242, from the vascular X-ray imaging device 270. When there is the request 206, the process advances to step 306. When there is no request 206, the process is terminated.

In step 306, the server 250 transmits at least one of the first information 241 or the second information 242 to the vascular X-ray imaging device 270. Then, the process is terminated.

Deletion of First Information

In this embodiment, the HIS server 254 deletes the first information 241 and stores the second information 242 in association with the patient information 245 immediately after the second information 242 is associated with the patient information 245, after a preset period of time has elapsed, or based on information 208 (see FIG. 10) indicating the end of treatment from the vascular X-ray imaging device 270. In this embodiment, the HIS server 254 deletes the first information 241 based on the information 208 indicating the end of treatment from the vascular X-ray imaging device 270 after associating the second information 242 with the patient information 245.

Figure 13:
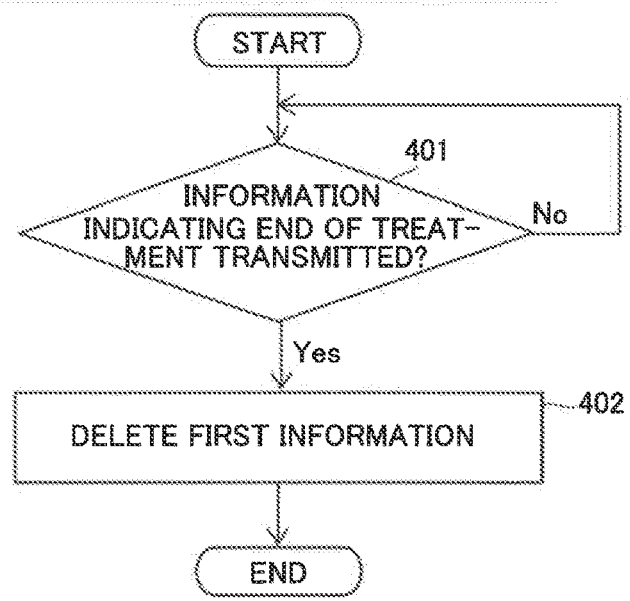
FIG. 13 is a flowchart showing a process to delete the first information.

A process to delete the first information 241 in a case in which the first information 241 is deleted based on the information 208 (see FIG. 10) indicating the end of treatment is now described with reference to FIG. 13.

In step 401, the server 250 determines whether or not the information 208 indicating the end of treatment has been transmitted from the vascular X-ray imaging device 270. When the server 250 receives the information 208 indicating the end of treatment from the vascular X-ray imaging device 270, the process advances to step 402. When the server 250 has not received the information 208 indicating the end of treatment from the vascular X-ray imaging device 270, the server 250 repeats the process of step 401.

In step 402, the server 250 deletes the first information 241. Then, the process is terminated.

Transmission of Second Information and CT Image or MRI Image

Figure 14:
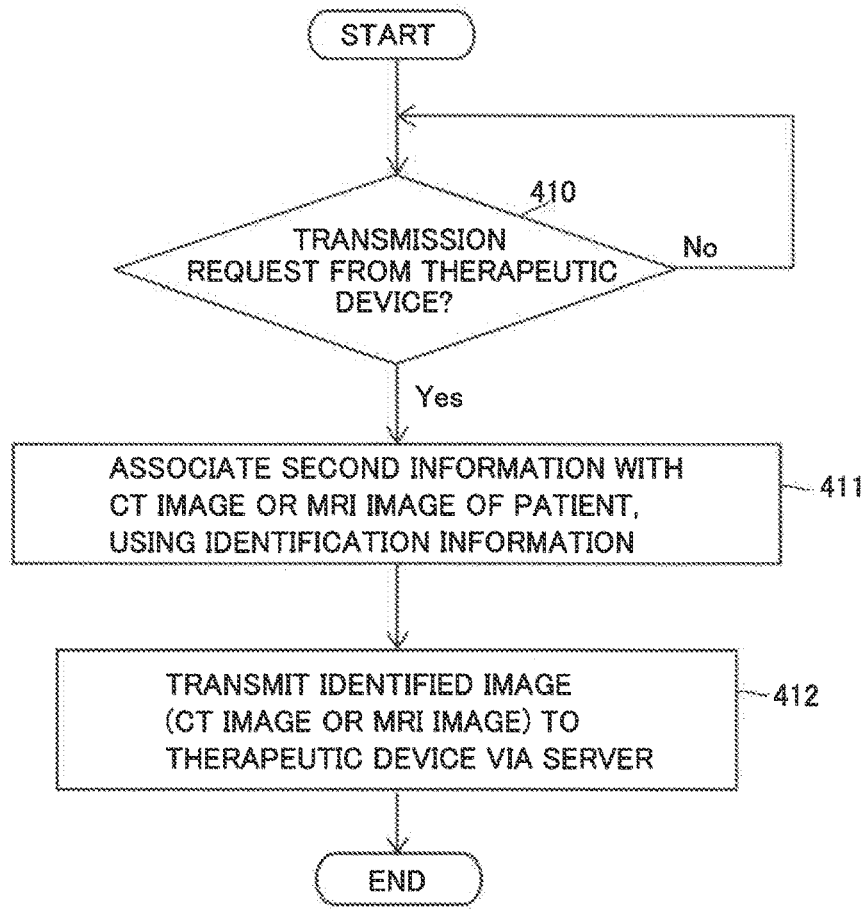
FIG. 14 is a flowchart showing a process to transmit the second information and a CT image or an MRI image.

A process of the server 250 to transmit the second information 242 and the CT image 6 or MRI image 7 of the patient 1 to the vascular X-ray imaging device 270 is now described with reference to FIG. 14.

In step 410, the DICOM server 253 determines whether or not there is the transmission request 207 for the image (CT image 6 or MRI image 7) from the vascular X-ray imaging device 270. When there is the image transmission request, the process advances to step 411. When there is no image transmission request, the process of step 410 is repeated. When the transmission request 207 is transmitted from the vascular X-ray imaging device 270, the identification information 245a is also transmitted.

Then, in step 411, the DICOM server 253 (server 250) associates the second information 242 with the CT image 6 or MRI image 7 of the patient 1, using the identification information 245a. Specifically, the DICOM server 253 that has received the transmission request 207 associates the second information 242 with the image (CT image 6 or MRI image 7) by identifying the image (CT image 6 or MRI image 7) of the patient 1 from the plurality of stored images (CT images 6 or MRI images 7) based on the identification information 245a.

Then, in step 412, the DICOM server 253 (server 250) transmits the identified image (CT image 6 or MRI image 7) to the vascular X-ray imaging device 270 via the RIS server 252. That is, the DICOM server 253 (server 250) transmits the CT image 6 or MRI image 7 of the patient 1 and the second information 242 to the vascular X-ray imaging device 270 based on the request 206 and the request 207 from the vascular X-ray imaging device 270. Then, the process is terminated.

Vascular Imaging Device

Figure 15:
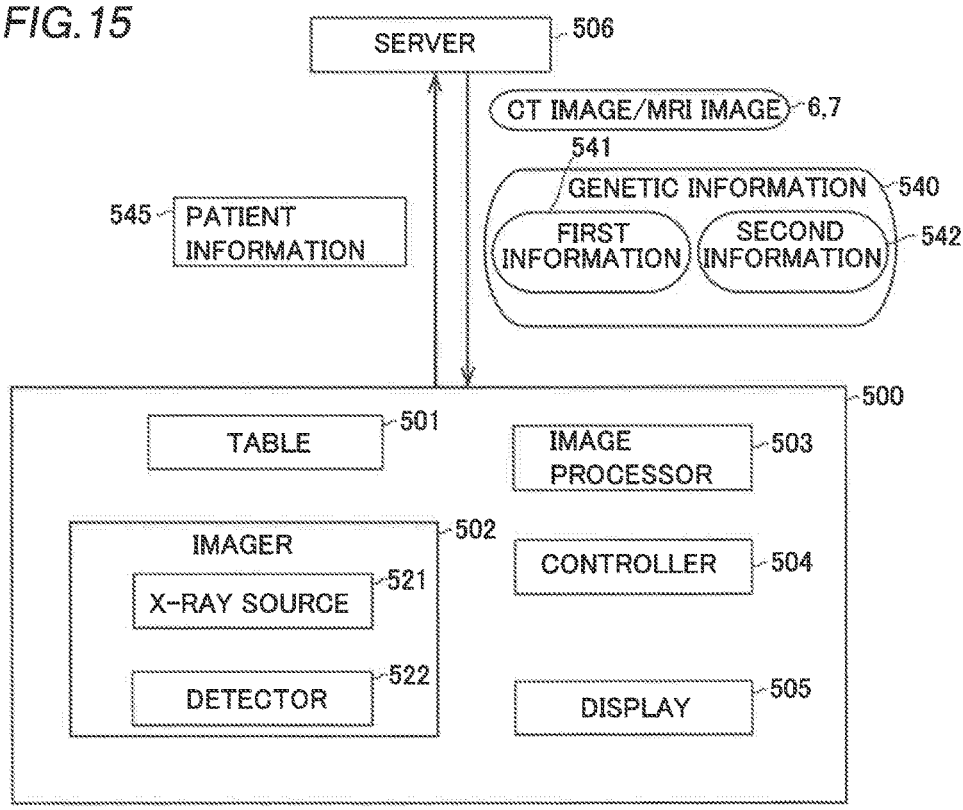
FIG. 15 is a block diagram showing the configuration of a vascular imaging device.

The vascular X-ray imaging device 270 (see FIG. 11) installed in the catheter lab 902 is a vascular imaging device 500 shown in FIG. 15, for example. A configuration example of the vascular imaging device 500 is described in detail below.

Configuration of Vascular Imaging Device

Figure 16:
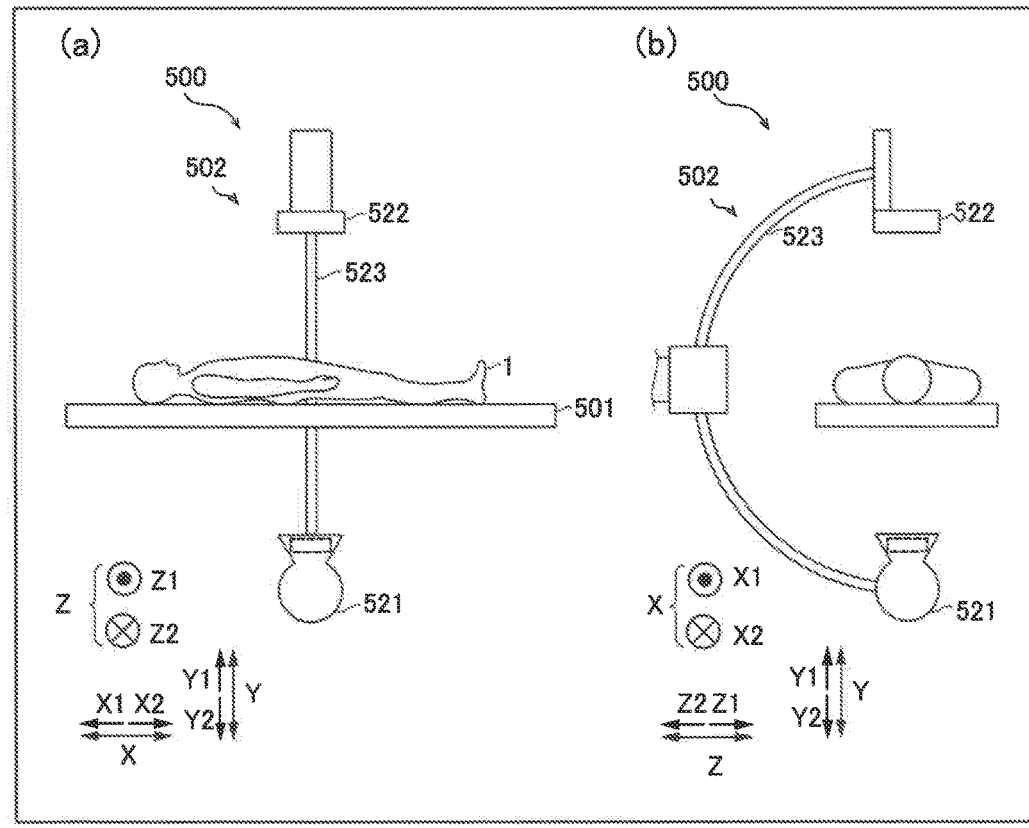
FIG. 16 at (A) and (B) are diagrams showing an example of the vascular imaging device.

As shown in FIGS. 15 and 16, the vascular imaging device 500 according to this embodiment includes a table 501 on which a patient 1 is placed, an imager 502 including an X-ray source 521 and a detector 522, an image processor 503, a controller 504, and a display 505.

The table 501 has a rectangular flat plate shape in a plan view. The patient 1 is placed on the table 501 such that the head-foot direction of the patient 1 is along the long side of the rectangle and the right-left direction of the patient 1 is along the short side of the rectangle. In this description, the head-foot direction of the patient 1 is defined as an X direction, the right-left direction of the patient 1 is defined as a Z direction, and a direction orthogonal to the X direction and the Z direction is defined as a Y direction.

The imager 502 irradiates the patient 1 with X-rays from the X-ray source 521 and detects the X-rays transmitted through the patient 1 with the detector 522.

As shown in FIG. 16 at (B), the X-ray source 521 is attached to the tip end of a C-shaped holder 523 on a first side. An X-ray tube drive (not shown) applies a voltage to the X-ray source 521 such that the X-ray source 521 can irradiate the patient 1 with X-rays. The X-ray source 521 includes a collimator capable of adjusting an X-ray irradiation field, which is the irradiation range of X-rays.

The detector 522 is attached to the tip end of the holder 523 on a second side. That is, the detector 522 is arranged on the side opposite to the X-ray source 521 with the table 501 being interposed between the detector 522 and the X-ray source 521. The detector 522 is arranged so as to face the X-ray source 521, and thus the detector 522 can detect the X-rays that have passed through the patient 1. The detector 522 includes a flat panel detector (FPD), for example.

As shown in FIG. 15, the image processor 503 includes a computer including a processor such as a graphics processing unit (GPU) or a field-programmable gate array (FPGA) configured for image processing. The image processor functions as an image processing device by executing an image processing program.

The image processor 503 generates a fluoroscopic image 520 (see FIG. 17) of the patient 1 based on a detection signal output from the detector 522.

The controller 504 includes a computer including a central processing unit (CPU), a read-only memory (ROM), a random access memory (RAM), etc.

The controller 504 acquires a CT image 6 or an MRI image 7 from a server 506. The server 506 has the same or similar configuration as the server 250 (see FIGS. 10 and 11), and thus detailed description thereof is omitted.

As shown in FIG. 15, the controller 504 acquires CT images 6 or MRI images 7 of the patient 1 undergoing fluoroscopic imaging from the server 506 based on patient information 545 of the patient 1 undergoing fluoroscopic imaging.

Figure 17:
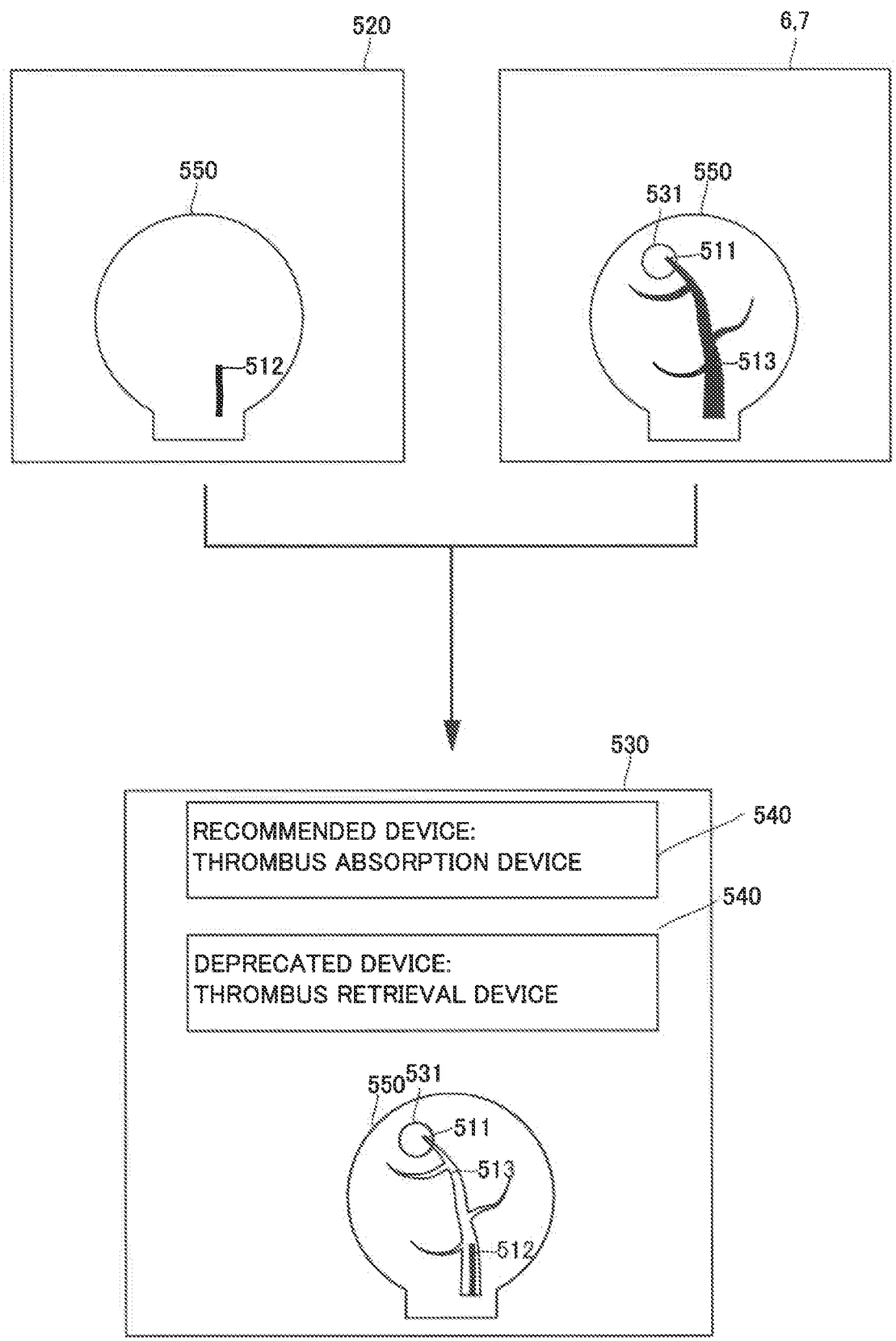
FIG. 17 is a diagram for illustrating generation of a superimposed image.

The controller 504 selects a CT image 6 or an MRI image 7 having the same spatial coordinates as the fluoroscopic image 520 generated by the image processor 503 from among the CT images 6 or MRI images 7 of the patient 1 undergoing fluoroscopic imaging. FIG. 17 is a schematic view showing a process to generate a superimposed image 530 of the head 550 of the patient 1. The controller 504 superimposes (stacks) the fluoroscopic image 520 on the acquired CT image 6 or MRI image 7 and controls the display 505 to display a superimposed image.

As shown in FIG. 17, when a treatment position (thrombus site) 511 is associated with the CT image 6 or the MRI image 7, the controller 504 controls the display 505 to display the treatment position 511 together with the superimposed image 530. In FIG. 17, the treatment position 511 is marked with a mark 531. The mark 531 may be a figure surrounding the treatment position 511, and an arrow may be displayed.

The controller 504 performs a control to acquire genetic information 540 that matches the patient information 545 of the patient 1 undergoing fluoroscopic imaging from the server 506. The genetic information 540 includes at least one of first information 541 or second information 542. The first information 541 is the same or similar information as the first information 41 (see FIG. 4). That is, the first information 541 includes the patient information 545 and information as to whether or not a genetic polymorphism is present. The second information 542 is the same or similar information as the second information 42 (see FIG. 4). That is, the second information 542 includes at least one of information 42a about the type of cerebral infarction, information 42b about the cerebral blood vessel of the patient 1, or information 42c indicating a treatment device recommended or deprecated for use in catheter treatment of the cerebral infarction of the patient 1.

The controller 504 performs a control to further display the genetic information 540 on the image obtained by superimposing the fluoroscopic image 520 on the CT image 6 or the MRI image 7 and displayed on the display 505. The controller 504 performs a control to display the genetic information 540 at a position that does not overlap the treatment position 511. As shown in FIG. 17, the position that does not overlap the treatment position 511 is a position that does not overlap the mark 531 when the mark 531 indicating the treatment position 511 is displayed.

The display 505 is a monitor provided in the vascular imaging device 500. As shown in FIG. 17, in the fluoroscopic image 520, a catheter 512 is clear, but a blood vessel 513 is not clear. Therefore, the CT image 6 or the MRI image 7 is superimposed such that the superimposed image 530 in which the catheter 512 and the blood vessel 513 have been superimposed is generated. As shown in FIG. 17, in the superimposed image 530, the pixel value of the blood vessel 513 is inverted in order to clarify the catheter 512. In FIG. 17, the blood vessel 513 is whitened to show that the pixel value of the blood vessel 513 is inverted. The pixel value of the catheter 512 may be inverted. On the superimposed image, the mark 531 indicating the treatment position 511 and the genetic information 540 are displayed. In FIG. 17, the genetic information 540 is represented by characters. The superimposed image 530, the treatment position 511, and the genetic information 540 are displayed on the display 505 provided in the vascular imaging device 500 such that a doctor or the like can confirm them during treatment. The displayed genetic information 540 is at least one of the first information 541 or the second information 542.

Flow of Diagnosis by Doctor or the Like

A doctor or the like captures the CT image 6 or the MRI image 7 when the patient 1 who has developed cerebral infarction is transported to a hospital.

In CT imaging, a patient is imaged from a plurality of directions while the imager is rotated and moved. As shown in FIG. 18 at (A), a plurality of pieces of two-dimensional image data are generated in CT imaging. FIG. 18 at (A) shows an image captured while the imager is moved in the head-foot direction (X direction). Then, three-dimensional image data can be generated by reconstructing a plurality of two-dimensional CT images 6 continuously captured as shown in FIG. 18 at (B). A desired CT image 6 can be obtained by cutting the three-dimensional data in an arbitrary direction. For example, when the blood vessel 513 extends along the head-foot direction, the three-dimensional image data reconstructed as shown in FIG. 18 at (C) may be cut in a direction parallel to the head-foot direction (X direction).

Three-dimensional image data can be generated by reconstructing MRI images 7. An image of the blood vessel 513 can be generated by cutting the generated three-dimensional image data in a direction in which the blood vessel extends.

The doctor or the like confirms the treatment position 511, which is a treatment position, from the CT image 6 or the MRI image 7 captured in an image interpretation room 901. The doctor or the like selects the treatment position 511 in the CT image 6 or the MRI image 7 such that the treatment position 511 is marked with the mark and is associated with the CT image 6 or the MRI image 7.

In the case of the CT image 6, the doctor or the like can determine the treatment position 511 by a CT value that is the absorption value of X-rays. In the case of cerebral infarction, a thrombus is formed in the blood vessel 513 at the treatment position 511. The thrombus absorbs more X-rays than the blood vessel to which a contrast medium has been administered so as to have a higher CT value, and thus the thrombus appears darker as compared with the blood vessel without a thrombus. The doctor or the like specifies the treatment position 511 from a difference in CT value.

In the case of the MRI image 7, the doctor or the like can determine the treatment position 511 from the detection signal. The detection signal is stronger in a location in which the blood flow is faster while the detection signal is weaker in a location in which the blood flow is slower, and thus the blood vessel with slower blood flow (cerebral infarction has been developed) appears darker as compared with other blood vessels. Therefore, the doctor or the like specifies the treatment position 511.

After imaging of the CT image 6 and MRI image 7 of the patient 1 is completed, the doctor or the like starts treatment to remove the thrombus. As shown in FIG. 17, when the doctor or the like starts fluoroscopic imaging for the treatment, the superimposed image 530 in which the fluoroscopic image 520 and the CT image 6 or the MRI image 7 have been superimposed, and the genetic information 540 are displayed on the display 505. As shown in FIG. 17, the treatment position 511 in the CT image 6 or the MRI image 7 is marked with the mark 531, and thus the treatment position 511 can be confirmed even when the doctor or the like who performs the treatment is different from a doctor or the like who performs diagnosis in the image interpretation room 901. The superimposed image 530 and the genetic information 540 are displayed on the display 505, and thus the doctor or the like can smoothly perform an operation.

The fluoroscopic imaging operation of the vascular imaging device 500 is now described with reference to FIG. 19.

In step 601, when receiving an input from a user, the vascular imaging device 500 starts vascular fluoroscopic imaging. When the vascular fluoroscopic imaging is started, the vascular imaging device 500 irradiates the patient 1 with X-rays from the X-ray source 521. The detector 522 detects the X-rays transmitted through the patient 1 and outputs detection signals.

In step 602, the image processor 503 generates the fluoroscopic image 520 based on the detection signals.

In step 603, the controller 504 performs a control to acquire the CT image 6 or the MRI image 7 having the same spatial position coordinates as the fluoroscopic image 520 generated in step 602 from the server 506.

In step 604, the controller 504 superimposes the fluoroscopic image 520 on the acquired CT image 6 or MRI image 7 and controls the display 505 to display the superimposed image.

In step 605, the controller 504 performs a control to acquire the genetic information 540 that matches the patient information 545 from the server.

In step 606, the controller 504 controls the display 505 to display the acquired genetic information 540 and the superimposed image 530 in which the CT image 6 or the MRI image 7 and the fluoroscopic image 520 have been superimposed.

Advantages of this Embodiment

In this embodiment, the following advantages are obtained.

As described above, the cerebral infarction treatment support system 100 according to this embodiment includes the detection device 10 configured to measure the biological sample 2 collected from the patient 1 and generate the first information 41 as to whether or not the biological sample 2 has the susceptibility gene for cerebral infarction, the display 30 arranged in at least one of the catheter lab 902 in which the vascular X-ray imaging device 70 is arranged or the image interpretation room 901 in which the image browsing terminal 80 for radiation diagnostic images or MRI images is arranged, and the image controller 20 configured or programmed to control the display 30, and the image controller 20 includes the receiver 21 configured to receive at least one of the first information 41 generated by the detection device 10 or the second information 42 related to the susceptibility gene generated based on the first information 41, and the video output 22 configured to output at least one of the received first information 41 or second information 42 to the display 30.

As described above, the cerebral infarction treatment support method according to this embodiment includes measuring the biological sample 2 collected from the patient 1 and generating the first information 41 as to whether or not the biological sample 2 has the susceptibility gene for cerebral infarction, receiving at least one of the generated first information 41 or the second information 42 related to the susceptibility gene generated based on the first information 41, and outputting at least one of the received first information 41 or second information 42 to the display 30, and the display 30 is arranged in at least one of the catheter lab 902 in which the vascular X-ray imaging device 70 is arranged or the image interpretation room 901 in which the image browsing terminal 80 for radiation diagnostic images or MRI images is arranged.

In the cerebral infarction treatment support system 100 and the cerebral infarction treatment support method according to this embodiment, with the above configuration, in the treatment of the cerebral infarction patient 1 in the acute phase, at least one of the first information 41 as to whether or not the patient 1 has the susceptibility gene for cerebral infarction or the second information 42 generated based on the first information 41 can be displayed on the display 30 (second display 82) arranged in the image interpretation room 901 in which the type of cerebral infarction is determined and the location of the thrombus is identified, for example. Thus, at least one of the first information 41 or the second information 42 is displayed during diagnosis for determining the type of cerebral infarction and identifying the location of the thrombus, for example, such that a doctor can determine the type of cerebral infarction, taking into consideration information based on the presence or absence of the susceptibility gene, which cannot be obtained from image information, in addition to the conventional image interpretation based on the CT image 6 and the MRI image 7. Furthermore, at least one of the first information 41 or the second information 42 is displayed during treatment on the display 30 (first display 72) arranged in the catheter lab 902 in which the patient 1 who has developed cerebral infarction is treated such that a doctor who actually performs treatment can select a treatment device for catheter treatment according to the type of cerebral infarction, taking into consideration the information based on the presence or absence of the susceptibility gene. Thus, it is possible to present support information useful for the doctor to identify the type of cerebral infarction during diagnosis or treatment of cerebral infarction in the acute phase.

In this embodiment, with the following configuration, further advantages are obtained.

That is, in the aforementioned embodiment, the image controller 20 is configured or programmed to receive at least the second information 42 and output it to the display 30, and the second information 42 includes at least one of the information 42a about the type of cerebral infarction, the information 42b about the cerebral blood vessel of the patient 1, or the information 42c indicating a treatment device recommended or deprecated for use in catheter treatment of the cerebral infarction of the patient 1. Accordingly, as the second information 42 derived based on the first information 41 as to whether or not the susceptibility gene for cerebral infarction is present, support information particularly useful for a doctor involved in diagnosis or treatment of cerebral infarction in the acute phase can be presented.

In the aforementioned embodiment, the detection device 10 is configured to assign the patient information 45 of the patient 1 from which the biological sample 2 has been collected to the first information 41, and the image controller 20 is configured or programmed to receive the image of the patient 1 to which the patient information 45 has been assigned, and output the image having the same patient information 45 and at least one of the first information 41 or the second information 42 to the display 30. Accordingly, the image used for treatment or diagnosis can be associated with the first information 41 and/or the second information 42 via the patient information 45. Therefore, even in an emergency such as the treatment or diagnosis of the cerebral infarction patient 1 in the acute phase, a doctor can be collectively and reliably provided with these images and information without using uncertain communication means such as oral communication.

In the aforementioned embodiment, the image controller 20 includes the first control device 71 of the vascular X-ray imaging device 70 installed in the catheter lab 902, and the display 30 includes the first display 72 installed in the catheter lab 902 and configured to display the X-ray image 73 captured by the vascular X-ray imaging device 70. Accordingly, the vascular X-ray imaging device 70 used when catheter treatment is performed can receive the first information 41 and/or the second information 42 and display them on the display 30. Therefore, it is not necessary to provide a dedicated device for displaying the first information 41 and/or the second information 42, and the system configuration can be simplified.

In the aforementioned embodiment, the first control device 71 is configured or programmed to output at least one of the received first information 41 or second information 42, and the X-ray image 73 of the patient 1 captured by the vascular X-ray imaging device 70 to the first display 72 during the catheter treatment of the patient 1 in the catheter lab 902. Accordingly, the first information 41 and/or the second information 42 can be displayed together with the X-ray image 73 showing the catheter during the catheter treatment. Therefore, the first information 41 and/or the second information 42 can be reliably presented to a doctor who actually performs the catheter treatment.

In the aforementioned embodiment, the image controller 20 includes the second control device 81 of the image browsing terminal 80 installed in the image interpretation room 901, and the display 30 includes the second display 82 installed in the image interpretation room 901 and configured to display the screen of the image browsing terminal 80. Accordingly, the image browsing terminal 80 in the image interpretation room 901 used to diagnose the patient 1 who has developed cerebral infarction can receive the first information 41 and/or the second information 42 and display it on the display 30. Therefore, it is not necessary to provide a dedicated device for displaying the first information 41 and/or the second information 42, and the system configuration can be simplified.

In the aforementioned embodiment, the second control device 81 is configured or programmed to receive at least one of the first information 41 or the second information 42 and the CT image 6 or the MRI image 7 of the patient 1, and output them to the second display 82 during the diagnosis of the patient 1 in the image interpretation room 901. Accordingly, during the diagnosis of the patient 1 who has developed cerebral infarction, the first information 41 and/or the second information 42 can be displayed together with the CT image 6 or the MRI image 7 used for the diagnosis. Therefore, the first information 41 and/or the second information 42 can be reliably presented to a doctor who actually identifies the type of cerebral infarction.

In the aforementioned embodiment, the cerebral infarction treatment support system 100 further includes the server 50 communicably connected to the detection device 10 and the image controller 20 and configured to store the first information 41, the server 50 is configured to generate the second information 42 based on the first information 41, and the image controller 20 is configured or programmed to receive at least the second information 42 from the server 50. Accordingly, based on the first information 41 generated by the detection device 10, the second information 42 can be automatically generated and presented to a doctor or the like during treatment or diagnosis. Therefore, it is possible to reliably present support information useful for the doctor involved in the diagnosis or treatment even in an emergency such as the treatment or diagnosis of the cerebral infarction patient 1 in the acute phase.

In the aforementioned embodiment, the server 50 includes at least one of the radiology information system server (RIS server 52) or the medical image management system server (DICOM server 53) connected to the in-hospital network. Accordingly, the second information 42 can be generated by the server (52 or 53) of the existing network constructed in the hospital. Furthermore, each server (52 or 53) described above handles radiographic images or medical images, and thus the images (the CT image 6, the MRI image 7, and the X-ray image 73 at the time of treatment) that a doctor refers to during the treatment or diagnosis of the cerebral infarction patient 1 and the second information 42 can be easily associated with each other, managed and provided.

In the aforementioned embodiment, the susceptibility gene for cerebral infarction includes the RNF213 p.R4810K genetic polymorphism. Accordingly, the first information 41 as to whether or not the RNF213 p.R4810K genetic polymorphism is present can be presented to a doctor. Based on this first information 41, a doctor or the like can obtain findings useful for treatment and diagnosis such as the fact that the type of cerebral infarction that the patient 1 has developed is significantly more likely to be atherothrombotic cerebral infarction, the fact that the vascular diameter of a major cerebral blood vessel tends to be small, and the fact that care should be taken when a thrombus retrieval device is used during catheter treatment due to the small vascular diameter, and even when used, it is preferable to use a thrombus retrieval device with a smaller diameter than usual.

In the aforementioned embodiment, the detection device 10 includes the gene amplification detection device configured to perform the gene amplification process on the biological sample 2 containing the specimen 2a containing blood or saliva collected from the patient 1 and the reaction solution 2c containing the component that suppresses the influence of the inhibitor in the specimen 2a. Accordingly, the detection device 10 can directly measure the biological sample 2 collected from the patient 1 and generate the first information 41 without the purification process to remove the inhibitor in the biological sample 2 and purify the gene. Therefore, as compared with a case in which the purification process is performed, a portion (purification process) of a preprocess for the measurement by the detection device 10 becomes unnecessary, and thus the first information 41 can be generated quickly. Therefore, the above configuration is particularly useful in that a doctor can be provided as early as possible with the first information 41 in an emergency such as the treatment or diagnosis of the cerebral infarction patient 1 in the acute phase.

In the aforementioned embodiment, the detection device 10 includes the gene amplification detection device configured to perform the real-time PCR technique to perform the labeling process with the labeling substance in the process of gene amplification. Accordingly, the first information 41 can be quickly generated as compared with a usual (non-real-time) PCR technique to perform amplification and then perform the labeling process. Therefore, the above configuration is particularly useful in that a doctor can be provided as early as possible with the first information 41 in an emergency such as the treatment or diagnosis of the cerebral infarction patient 1 in the acute phase.

In the aforementioned embodiment, the cerebral infarction treatment support method further includes assigning the patient information 45 of the patient 1 to the first information 41 generated by the biological sample 2 collected from the patient 1 transported as an emergency, and at least one of the received first information 41 or second information 42 is displayed together with the patient information 45 on the display 30 at least by the time of treatment of the patient 1. Accordingly, even in an emergency such as the treatment of the cerebral infarction patient 1 in the acute phase, the patient 1 can be identified based on the patient information 45, and the first information 41 can be reliably presented together with the patient information 45 to a doctor.

EXAMPLES

A result (case) of confirming the presence or absence of the RNF213 p.R4810K polymorphism for a patient who has developed cerebral infarction by the present inventors is described.

The present inventors captured an MRI image and a magnetic resonance angiography (MRA) image for one patient who was raced to the hospital, and confirmed that he/she had developed cerebral infarction in the major cerebral artery.

The present inventors treated the patient to remove a thrombus in the blood vessel using a thrombus suction device 5b<cerebral infarction treatment 1>. After the cerebral infarction treatment 1, reocclusion was observed in the patient's blood vessel. Therefore, the present inventors performed treatment to dilate the blood vessel by placing a stent in the blood vessel using a percutaneous angioplasty device 5c<cerebral infarction treatment 2>. After the cerebral infarction treatment 2, reocclusion was observed in the patient's blood vessel, and thus the present inventors performed treatment to dilate the blood vessel again using the percutaneous angioplasty device 5c<cerebral infarction treatment 3>. Furthermore, this patient was examined for the RNF213 p.R4810K genetic polymorphism. As a result of the examination, the patient had the RNF213 p.R4810K genetic polymorphism.

It is known that the cause of reocclusion of a blood vessel is related to intracranial artery stenosis in which the blood vessel narrows, but in this case, intracranial artery stenosis was not clear. Therefore, as a result of the examination by the present inventors, the patient with the RNF213 p.R4810K genetic polymorphism tends to have a thinner blood vessel (fragility of the intracranial vascular endothelium) than a patient without this genetic polymorphism, and thus it has been concluded that vascular endothelial damage may have occurred due to physical stimulation during thrombus retrieval with a stent, leading to reocclusion of the blood vessel. Thus, it has been confirmed that the patient with the RNF213 p.R4810K genetic polymorphism and fragile vascular endothelium has a relatively high risk of reocclusion of the blood vessel.

Therefore, as in the aforementioned embodiment, the information as to whether or not the patient has the RNF213 p.R4810K genetic polymorphism is provided in advance before treatment such that it is possible to advise a doctor that care should be taken to prevent direct contact of a treatment device with a blood vessel and not to provide physical stimulation to the blood vessel even when a treatment device that does not contact the blood vessel is used.

MODIFIED EXAMPLES

The embodiment disclosed this time must be considered as illustrative in all points and not restrictive. The scope of the present invention is not shown by the above description of the embodiment but by the scope of claims for patent, and all modifications (modified examples) within the meaning and scope equivalent to the scope of claims for patent are further included.

For example, while the example in which the second information 42 includes at least one of the information 42a about the type of cerebral infarction, the information 42b about the cerebral blood vessel, or the device information 42c has been shown in the aforementioned embodiment, the present invention is not limited to this. The second information 42 may include information other than the aforementioned information as long as it is derived from the first information 41.

While the example in which the patient information 45 is assigned to the first information 41 has been shown in the aforementioned embodiment, the present invention is not limited to this. In the present invention, the patient information 45 may not be assigned to the first information 41.

While the example in which the images such as the CT image 6, the MRI image 7, and the X-ray image 73, and at least one of the first information 41 or the second information 42 are displayed on the display 30 has been shown in the aforementioned embodiment, the present invention is not limited to this. At least one of the first information 41 or the second information 42 may be displayed on the display 30 without displaying the images.

While the example in which the detection device 10 is a direct PCR device has been shown in the aforementioned embodiment, the present invention is not limited to this. The detection device 10 may perform a PCR process on the biological sample 2 prepared by performing the purification process to purify DNA from the specimen 2a.

While the example in which the detection device 10 performs the real-time PCR technique has been shown in the aforementioned embodiment, the present invention is not limited to this. The detection device 10 may be configured to perform a non-real-time PCR technique.

Aspects

It will be appreciated by those skilled in the art that the exemplary embodiments described above are specific examples of the following aspects.

(Item 1)

A cerebral infarction treatment support system comprising:

a detection device configured to measure a biological sample collected from a patient, the detection device being configured to generate first information as to whether or not the biological sample has a susceptibility gene for cerebral infarction;

a display arranged in at least one of a catheter lab in which a vascular X-ray imaging device is arranged or an image interpretation room in which an image browsing terminal for a radiation diagnostic image or an MRI image is arranged; and an image controller configured or programmed to control the display; wherein the image controller includes:

a receiver configured to receive at least one of the first information generated by the detection device or second information related to the susceptibility gene generated based on the first information; and a video output configured to output at least one of the received first information or second information to the display.

(Item 2)

The cerebral infarction treatment support system according to item 1, wherein the image controller is configured or programmed to receive and output at least the second information to the display; and the second information includes at least one of information about a type of cerebral infarction, information about a cerebral blood vessel of the patient, or information indicating a treatment device recommended or deprecated for use in catheter treatment of cerebral infarction of the patient.

(Item 3)

The cerebral infarction treatment support system according to item 1 or 2, wherein the detection device is configured to assign patient information of the patient from which the biological sample has been collected to the first information; and the image controller is configured or programmed to:

receive an image of the patient to which the patient information has been assigned; and output the image having the same patient information and at least one of the first information or the second information to the display.

(Item 4)

The cerebral infarction treatment support system according to any one of items 1 to 3, wherein the image controller includes a first control device of the vascular X-ray imaging device installed in the catheter lab; and the display includes a first display installed in the catheter lab, the first display being configured to display an X-ray image captured by the vascular X-ray imaging device.

(Item 5)

The cerebral infarction treatment support system according to item 4, wherein the first control device is configured or programmed to output at least one of the received first information or second information, and the X-ray image of the patient captured by the vascular X-ray imaging device to the first display during catheter treatment of the patient in the catheter lab.

(Item 6)

The cerebral infarction treatment support system according to any one of items 1 to 5, wherein the image controller includes a second control device of the image browsing terminal installed in the image interpretation room; and the display includes a second display installed in the image interpretation room, the second display being configured to display a screen of the image browsing terminal.

(Item 7)

The cerebral infarction treatment support system according to item 6, wherein the second control device is configured or programmed to receive and output at least one of the first information or the second information, and a CT image or the MRI image of the patient to the second display during diagnosis of the patient in the image interpretation room.

(Item 8)

The cerebral infarction treatment support system according to any one of items 1 to 7, further comprising:

a server communicably connected to the detection device and the image controller, the server being configured to store the first information; wherein the server is configured to generate the second information based on the first information; and the image controller is configured or programmed to receive at least the second information from the server.

(Item 9)

The cerebral infarction treatment support system according to item 8, wherein the server includes at least one of a radiology information system server or a medical image management system server, each of which is connected to an in-hospital network.

(Item 10)

The cerebral infarction treatment support system according to any one of items 1 to 9, wherein the susceptibility gene for cerebral infarction includes an RNF213 p.R4810K genetic polymorphism.

(Item 11)

The cerebral infarction treatment support system according to any one of items 1 to 10, wherein the detection device includes a gene amplification detection device configured to perform a gene amplification process on the biological sample containing a specimen that contains blood or saliva collected from the patient, the biological sample containing a reaction solution that contains a component that suppresses an influence of an inhibitor in the specimen.

(Item 12)

The cerebral infarction treatment support system according to any one of items 1 to 11, wherein the detection device includes a gene amplification detection device configured to perform a real-time PCR technique to perform a labeling process with a labeling substance in a process of gene amplification.

(Item 13)

A cerebral infarction treatment support method comprising:

measuring a biological sample collected from a patient and generating first information as to whether or not the biological sample has a susceptibility gene for cerebral infarction;

receiving at least one of the generated first information or second information related to the susceptibility gene generated based on the first information; and outputting at least one of the received first information or second information to a display; wherein the display is arranged in at least one of a catheter lab in which a vascular X-ray imaging device is arranged or an image interpretation room in which an image browsing terminal for a radiation diagnostic image or an MRI image is arranged.

(Item 14)

The cerebral infarction treatment support method according to item 13, further comprising:

assigning patient information of the patient to the first information generated by the biological sample collected from the patient transported as an emergency; wherein at least one of the received first information or second information is displayed together with the patient information on the display at least by a time of treatment of the patient.

DESCRIPTION OF REFERENCE NUMERALS

1: patient
2: biological sample
2a: specimen
2c: reaction solution
5: treatment device
6: CT image
7: MRI image
10: detection device
20: image controller
21: receiver
22: video output
30: display
41: first information
42: second information
42a: information about type of cerebral infarction
42b: information about cerebral blood vessel of patient
42c: device information (information indicating treatment device)
45: patient information
50: server
52: server
52: RIS server (radiology information system server)
53: DICOM server (medical image management system server)
70: vascular X-ray imaging device
71: first control device
72: first display
73: X-ray image
80: image browsing terminal
81: second control device
82: second display
100: cerebral infarction treatment support system
901: image interpretation room
902: catheter lab

The invention claimed is:

1. A cerebral infarction treatment support system comprising:

a detection device configured to measure a biological sample collected from a patient, the detection device being configured to generate first information as to whether or not the biological sample has a susceptibility gene for cerebral infarction;

a display arranged in at least one of a catheter lab in which a vascular X-ray imaging device is arranged or an image interpretation room in which an image browsing terminal for a radiation diagnostic image or an MRI image is arranged; and an image controller configured or programmed to control the display; wherein the image controller includes:

a receiver configured to receive at least one of the first information generated by the detection device or second information related to the susceptibility gene generated based on the first information; and a video output configured to output at least one of the received first information or second information to the display.

2. The cerebral infarction treatment support system according to claim 1, wherein
the image controller is configured or programmed to receive and output at least the second information to the display; and
the second information includes at least one of information about a type of cerebral infarction, information about a cerebral blood vessel of the patient, or information indicating a treatment device recommended or deprecated for use in catheter treatment of cerebral infarction of the patient.

3. The cerebral infarction treatment support system according to claim 1, wherein
the detection device is configured to assign patient information of the patient from which the biological sample has been collected to the first information; and
the image controller is configured or programmed to:
receive an image of the patient to which the patient information has been assigned; and
output the image having the same patient information and at least one of the first information or the second information to the display.

4. The cerebral infarction treatment support system according to claim 1, wherein
the image controller is provided in the vascular X-ray imaging device installed in the catheter lab; and
the display includes a first display installed in the catheter lab, the first display being configured to display an X-ray image captured by the vascular X-ray imaging device.

5. The cerebral infarction treatment support system according to claim 4, wherein the image controller is configured or programmed to output at least one of the received first information or second information, and the X-ray image of the patient captured by the vascular X-ray imaging device to the first display during catheter treatment of the patient in the catheter lab.

6. The cerebral infarction treatment support system according to claim 1, wherein
the image controller is provided in the image browsing terminal installed in the image interpretation room; and
the display includes a second display installed in the image interpretation room, the second display being configured to display a screen of the image browsing terminal.

7. The cerebral infarction treatment support system according to claim 6, wherein the image controller is configured or programmed to receive and output at least one of the first information or the second information, and a CT image or the MRI image of the patient to the second display during diagnosis of the patient in the image interpretation room.

8. The cerebral infarction treatment support system according to claim 1, further comprising:
a server communicably connected to the detection device and the image controller, the server being configured to store the first information; wherein
the server is configured to generate the second information based on the first information; and
the image controller is configured or programmed to receive at least the second information from the server.

9. The cerebral infarction treatment support system according to claim 8, wherein the server includes at least one of a radiology information system server or a medical image management system server, each of which is connected to an in-hospital network.

10. The cerebral infarction treatment support system according to claim 1, wherein the susceptibility gene for cerebral infarction includes an RNF213 p.R4810K genetic polymorphism.

11. The cerebral infarction treatment support system according to claim 1, wherein the detection device is configured to perform a gene amplification process on the biological sample containing a specimen that contains blood or saliva collected from the patient, the biological sample containing a reaction solution that contains a component that suppresses an influence of an inhibitor in the specimen.

12. The cerebral infarction treatment support system according to claim 1, wherein the detection device is configured to perform a real-time PCR technique to perform a labeling process with a labeling substance in a process of gene amplification.

13. A cerebral infarction treatment support method comprising:
measuring a biological sample collected from a patient and generating first information as to whether or not the biological sample has a susceptibility gene for cerebral infarction;
receiving at least one of the generated first information or second information related to the susceptibility gene generated based on the first information; and
outputting at least one of the received first information or second information to a display; wherein
the display is arranged in at least one of a catheter lab in which a vascular X-ray imaging device is arranged or an image interpretation room in which an image browsing terminal for a radiation diagnostic image or an MRI image is arranged.

14. The cerebral infarction treatment support method according to claim 13, further comprising:
assigning patient information of the patient to the first information generated by the biological sample collected from the patient transported as an emergency; wherein
at least one of the received first information or second information is displayed together with the patient information on the display at least by a time of treatment of the patient.

* * * * *